US008962680B2

(12) United States Patent
Forbes et al.

(10) Patent No.: US 8,962,680 B2
(45) Date of Patent: *Feb. 24, 2015

(54) METHODS AND COMPOSITIONS FOR TREATING HIV-ASSOCIATED DIARRHEA

(75) Inventors: William Forbes, Raleigh, NC (US); Enoch Bortey, Chapel Hill, NC (US); Steven King, Moss Beach, CA (US); Pravin Chaturvedi, Andover, MA (US)

(73) Assignees: Salix Pharmaceuticals, Ltd., Raleigh, NC (US); Napo Pharmaceuticals, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/285,397

(22) Filed: Oct. 31, 2011

(65) Prior Publication Data
US 2012/0184605 A1 Jul. 19, 2012

Related U.S. Application Data

(60) Provisional application No. 61/408,622, filed on Oct. 31, 2010, provisional application No. 61/409,335, filed on Nov. 2, 2010, provisional application No. 61/416,249, filed on Nov. 22, 2010, provisional application No. 61/434,379, filed on Jan. 19, 2011.

(51) Int. Cl.
A61K 31/352 (2006.01)
A61P 1/12 (2006.01)
A61P 1/00 (2006.01)
A61K 31/353 (2006.01)
A61K 31/05 (2006.01)

(52) U.S. Cl.
CPC .............. A61K 31/353 (2013.01); A61K 31/05 (2013.01)
USPC ........................................................ 514/486

(58) Field of Classification Search
None
See application file for complete search history.

(56) References Cited

U.S. PATENT DOCUMENTS

| | | | |
|---|---|---|---|
| 5,211,944 | A | 5/1993 | Tempesta et al. |
| 5,494,661 | A | 2/1996 | Tempesta et al. |
| 7,323,195 | B2 | 1/2008 | Rozhon et al. |
| 7,341,744 | B1 | 3/2008 | Rozhon et al. |
| 7,556,831 | B2 | 7/2009 | Quart et al. |
| 7,928,115 | B2 | 4/2011 | Forbes et al. |
| 8,067,041 | B2 | 11/2011 | Quart et al. |
| 8,574,634 | B2 | 11/2013 | Rozhon et al. |
| 2004/0071793 | A1 | 4/2004 | Bobrowski |
| 2007/0254050 | A1* | 11/2007 | Quart et al. ................... 424/725 |
| 2008/0025966 | A1 | 1/2008 | Currie et al. |
| 2008/0031984 | A1 | 2/2008 | Quart et al. |
| 2009/0148397 | A1 | 6/2009 | Rozhon et al. |
| 2010/0092479 | A1 | 4/2010 | Johansen et al. |
| 2011/0158942 | A1 | 6/2011 | Weber et al. |
| 2012/0107370 | A1 | 5/2012 | Forbes et al. |
| 2012/0128797 | A1 | 5/2012 | Quart et al. |
| 2012/0189720 | A1 | 7/2012 | Quart et al. |
| 2012/0202876 | A1 | 8/2012 | Verkman et al. |
| 2014/0011869 | A1 | 1/2014 | Rozhon et al. |
| 2014/0163096 | A1 | 6/2014 | Golden et al. |
| 2014/0294903 | A1 | 10/2014 | Forbes et al. |

FOREIGN PATENT DOCUMENTS

| | | |
|---|---|---|
| WO | WO92/06695 | 4/1992 |
| WO | WO00/47062 | 8/2000 |
| WO | WO2007/130882 | 11/2007 |
| WO | WO2007/130892 | 11/2007 |
| WO | WO2007/130893 | 11/2007 |
| WO | WO2011/024049 | 3/2011 |
| WO | WO2011/044137 | 4/2011 |
| WO | WO-2011044167 A1 | 4/2011 |

OTHER PUBLICATIONS

Holodniy et al. in American Journal of Gastroenterology 1999; 94;3267-3272.*
McMahan et al. in Alimentary Pharmacology & Therapeutics, 25, 7, 2007.*
Goodman and Gilman's The Pharmacological Basis of Therapeutics (Tenth Edition (2001)), McGraw Hill, Chapter I, pp. 3-29.*
Crutchley et al., Crofelemer, a novel agent for treatment of secretory diarrhea, Annals of Pharmacotherapy, 44(5):878-884, 2010.
DiCesare et al., "A double blind, randomized, placebo-controlled study of SP-303 (Provir) in the symptomatic treatment of acute diarrhea among travelers to Jamaica and Mexico", Am. J. Gastroenterol., 97(10): 2585-2588, 2002.
Fischer et al., "A novel extract SB-300 from the stem bark latex of Croton lechleri inhibits CFTR-mediated chloride secretion in human colonic epithelial cells", Journal of Ethnopharmacology, 93: 351-357, 2004.
U.S. Appl. No. 14/276,231, Rozhon et al.
Bardhan PK, et al., Safety and efficacy of a novel anti-secretory anti-diarrhel agent Crofelemer (NP-303), in treatment of adult infectious diarrhea and cholera, with or without the use of antibiotics. 13th International Conference on Emerging Infectious Diseases of the Pacific Rim; Kolkata, India pp. 18-19, Apr. 6-9, 2009.
Barrett KE, Keely SJ. Chloride secretion by the intestinal epithelium: molecular basis and regulatory aspects. Annu Rev Physiol. 2000;62:535-72.
Caputo A, et al., TMEM16A, A Membrane Protein Associated with Calcium-Dependent Chloride Channel Activity. Science 2008 322: 590-591.
De La Fuente R, et al., Small-molecule screen identifies inhibitors of a human intestinal calcium-activated chloride channel. Mol Pharmacol. 2008; 73:758-768.

(Continued)

Primary Examiner — Dennis Heyer
(74) Attorney, Agent, or Firm — McCarter & English, LLP; Jonathan M. Sparks; Marcie B. Clarke

(57) ABSTRACT

Presented herein are methods for treating diarrhea by administering to a patient in need thereof, an inhibitor of chloride-ion transport in an amount sufficient to treat diarrhea. Treatment of diarrhea includes the treatment of the diarrhea as well as the pain, abdominal discomfort and other symptoms associated with diarrhea. In one embodiment, the inhibitor of chloride-ion transport is crofelemer.

27 Claims, 3 Drawing Sheets

(56) References Cited

OTHER PUBLICATIONS

Field M. Intestinal ion transport and the pathophysiology of diarrhea. J. Clin Invest. 2003; 111:931-943.
Gabriel SE, et al., A novel plant-derived inhibitor of cAMP-mediated fluid and chloride secretion. Am J. Physiol. 1999; 276:G58-G63.
Goodman & Gilman. The Pharmacological basis of Therapeutics. 9th edition. Interamericana 1996. México, p. 47.
Gyömörey K, et al., Non-CFTR chloride channels likely contribute to secretion in the murine small intestine. Pflugers Arch. 2001;443 Suppl 1:S103-6.
Hartzell C, et al., Calcium-activated chloride channels. Annu Rev. Physiol. 2005.67:719-758.
Jones K. Review of sangre de drago (*Croton lechleri*)—a South American tree sap in the treatment of diarrhea, inflammation, insect bites, viral infections, and wounds: traditional uses to clinical research. J Altern Complement Med. Dec. 2003;9(6):877-96.
Kidd JF, et al., Intracellular Ca2+ and Cl− channel activation in secretory cells. Annu Rev Physiol. 2000;62:493-513.
Lorrot M, et al., How do the rotavirus NSP4 and bacterial enterotoxins lead differently to diarrhea? Virol J. Mar. 21, 2007;4:31.
Ma T, et al., Thiazolidinone CFTR inhibitor identified by high-throughput screening blocks cholera toxin-induced intestinal fluid secretion. J Clin Invest. Dec. 2002;110(11):1651-8.
Manabe et al., Emerging Pharmacologic Therapies for Irritable Bowel Syndrome, Curr. Gastroenterol. Rep., 12(5):408-416, 2010.
Morris AP, et al., NSP4 elicits age-dependent diarrhea and Ca(2+)mediated I(−) influx into intestinal crypts of CF mice. Am J Physiol. Aug. 1999;277(2 Pt 1):G431-44.
Muanprasat C, et al., Discovery of glycine hydrazide pore-occluding CFTR inhibitors: mechanism, structure-activity analysis, and in vivo efficacy. J Gen Physiol. Aug. 2004;124(2):125-37.
Risco E, et al., Immunomodulatory activity and chemical characterisation of sangre de drago (dragon's blood) from *Croton lechleri*. Planta Med. Sep. 2003;69(9):785-94.
Rossi D, et al., Evaluation of the mutagenic, antimutagenic and antiproliferative potential of *Croton lechleri* (Muell. Arg.) latex. Phytomedicine. Mar. 2003;10(2-3):139-44.
Rufo PA, et al., Diarrhea-associated HIV-1 APIs potentiate muscarinic activation of Cl-secretion by T84 cells via prolongation of cytosolic Ca2+ signaling. Am J Physiol Cell Physiol. May 2004;286(5):C998-C1008.
Schroeder BC, et al., Expression cloning of TMEM16A as a calcium-activatet chloride channel subunit. Cell. Sep. 19, 2008;134(6):1019-29.
Schultheiss G, et al., Histamine-induced ion secretion across rat distal colon: involvement of histamine H1 and H2 receptors. Eur J Pharmacol. Sep. 28, 2006;546(1-3):161-70.
Schultheiss G, et al., Muscarinic receptor stimulation activates a Ca(2+)-dependent Cl(−) conductance in rat distal colon. J Membr Biol. Apr. 2005;204(3):117-27.
Sharma A, et al., Crofelemer improves acute diarrhea symptoms, in Proceedings of the 48th Annual Interscience Conference on Antimicrobial Agents and Chemotherapy; Oct. 25-28, 2008; Washington DC. American Society for Microbiology, Washington DC.
Sonawane ND, et al., Lectin conjugates as potent, nonabsorbable CFTR inhibitors for reducing intestinal fluid secretion in cholera. Gastroenterology. Apr. 2007;132(4):1234-44.
Sonawane ND, et al., Luminally active, nonabsorbable CFTR inhibitors as potential therapy to reduce intestinal fluid loss in cholera. FASEB J. Jan. 2006;20(1):130-2.
Sonawane ND, et al., Nanomolar CFTR inhibition by pore-occluding divalent polyethylene glycol-malonic acid hydrazides. Chem Biol. Jul. 21, 2008;15(7):718-28.
Takahashi A, et al., Mechanisms of chloride secretion induced by thermostable direct haemolysin of *Vibrio parahaemolyticus* in human colonic tissue and a human intestinal epithelial cell line. J Med Microbiol. Sep. 2000;49(9):801-10.
Thiagarajah JR, Verkman AS. New drug targets for cholera therapy. Trends Pharmacol Sci. Apr. 2005;26(4):172-5.
Tkach SM, et al., Contemporary recommendations for managing patients with irritable bowel syndrome based on data from evidence-based medicine. Contemporary gastroenterology Kyiv, 2011. No. 5(61) pp. 98-107.
Tradtrantip L, et al., Crofelemer, an antisecretory antidiarrheal proanthocyanidin oligomer extracted from *Croton lechleri*, targets two distinct intestinal chloride channels. Mol Pharmacol. Jan. 2010;77(1):69-78.
Ubillas R, et al., SP-303, an antiviral oligomeric proanthocyanidin from the latex of *Croton lechleri* (Sangre de Drago). Phytomedicine. Sep. 1994;1(2):77-106.
Bardhan PK, et al., Safety and efficacy of a novel anti-secretory anti-diarrheal agent Crofelemer (NP-303), in treatment of adult infectious diarrhea and cholera, with or without the use of antibiotics. 13th International Conference on Emerging Infectious Diseases of the Pacific Rim; Kolkata, India pp. 18-19, Apr. 6-9, 2009.
Mangel et al., Evaluation of Crofelemer in the Treatment of Diarrhea-Predominant Irritable Bowel Syndrome Patients Digestion, 2008, 78:180-186.
U.S. Appl. No. 08/559,396, Rozhon et al.
U.S. Appl. No. 08/730,772, Rozhon et al.
U.S. Appl. No. 09/066,989, Rozhon et al.
U.S. Appl. No. 11/998,170, Rozhon et al.
U.S. Appl. No. 11/998,171, Rozhon et al.
U.S. Appl. No. 14/023,598, Rozhon et al.
U.S. Appl. No. 07/916,311, Tempesta et al.
U.S. Appl. No. 07/596,893, Tempesta et al.
U.S. Appl. No. 13/840,861, Golden et al.

\* cited by examiner

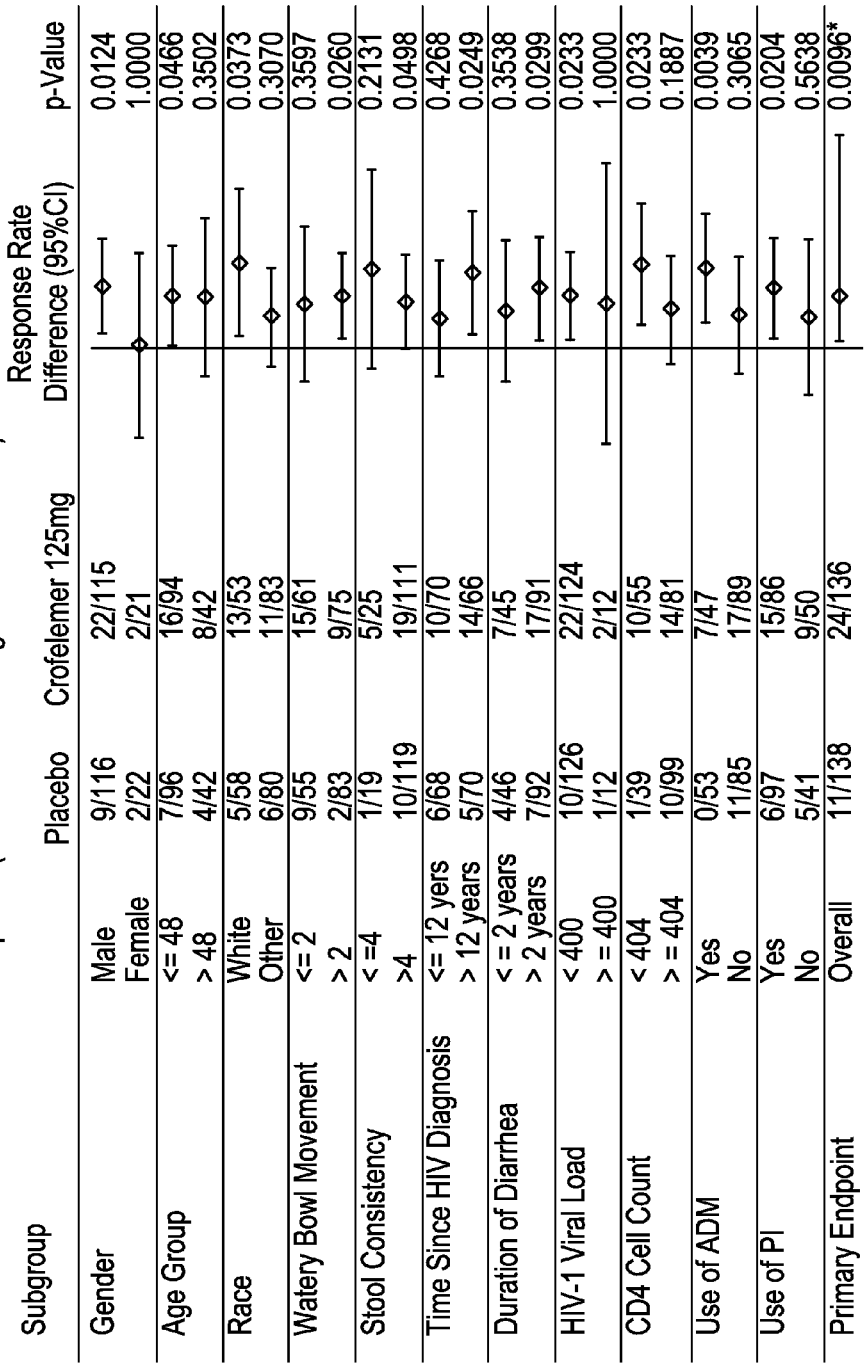

METHODS AND COMPOSITIONS FOR TREATING HIV-ASSOCIATED DIARRHEA

RELATED APPLICATIONS

This application claims the benefit of U.S. Provisional Application No. 61/408,622, filed Oct. 31, 2010; U.S. Provisional Application No. 61/409,335, filed Nov. 2, 2010; U.S. Provisional Application No. 61/416,249, filed Nov. 22, 2010; and U.S. Provisional Application No. 61/434,379, filed Jan. 19, 2011. The entire contents of each of these applications is hereby incorporated in herein by reference.

BACKGROUND

Diarrhea remains an important problem for HIV-infected subjects in the highly active antiretroviral therapy (HAART) era, impacting negatively on quality of life, despite the extensive use of anti-diarrheals. Causes are many and include HIV enteropathy, overgrowth of unusual microbial agents, common enteric pathogens malignancy, and adverse effects of HAART therapy itself (Kartalija 1999).

While definitions and methods of reporting vary, it is estimated that around half of all HIV-AIDS subjects will have diarrhea at some point during their illness. Although the incidence of diarrhea did not change during the introduction of HAART, the etiologies of diarrhea changed significantly with an increase of noninfectious causes and a decrease in opportunistic infectious causes.

Managing diarrhea will assist in improving overall efficacy of anti-viral drug therapies, as well as quality of life, and controlling weight loss in HIV-positive subjects. Diarrhea may result in reduced antiretroviral compliance and/or necessitate switching ARV regimens. Diarrhea has also been associated with reduced antiretroviral drug levels, suggesting that adequate treatment will improve the absorption of ARV medication. On a population-wide basis, adherence to drug treatment regimens and maintenance of adequate ARV levels are important for minimizing the development of drug resistant strains of the virus. Therefore, drug-related diarrhea in HIV-positive subjects represents an important and unmet clinical need requiring more effective management. Currently prescribed therapies are only partially effective or are plagued by unacceptable side effects such as constipation and the potential for addiction. The development of a drug for the treatment of HIV-associated diarrhea with a low potential for drug-drug interactions, effects on drug metabolism, or abuse potential would provide an important benefit for HIV-infected subjects.

SUMMARY

Disclosed herein are methods of preventing, ameliorating and/or treating diarrhea. In one embodiment, the methods presented herein prevent, ameliorate or treat HIV-associated diarrhea and highly active antiretroviral therapy (HAART) associated diarrhea.

In one aspect, presented herein are methods of treating HIV associated diarrhea or highly active antiretroviral therapy (HAART) associated diarrhea in an HIV positive subject, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer to a subject in need thereof.

In one aspect, presented herein are methods of treating stool consistency in an HIV positive subject, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer to a subject in need thereof.

In one aspect, presented herein are methods of improving stool consistency in an HIV positive subject, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer to a subject in need thereof.

In one aspect, presented herein are methods of alleviating watery diarrhea in an HIV positive subject, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer to a subject in need thereof.

In one aspect, presented herein are methods of decreasing the number of bowel movements per day in an HIV positive subject, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer to a subject in need thereof.

In one embodiment, the administering is from between about 1 month and about 5 months. In one embodiment, the administering is from between about 1 month and about 6 months. In one embodiment, the administering comprises about 6 months. In another embodiment, the administering comprises 6 months or longer.

In one embodiment, the administering is from between about 3 days and 5 months. In one embodiment, the administering is from between about 3 days and 6 months.

In one embodiment, improvement of symptoms begins on day 3.

In one embodiment, improvement of symptoms increases with a longer duration of administration after day 3.

In one embodiment, the subject is of Caucasian or Hispanic descent.

In one embodiment, the crofelemer is administered for at least 8 days.

In one embodiment, the crofelemer is administered from between 8 days and 24 weeks or 8 days and 26 weeks.

In one embodiment, a subject is considered treated if the subject demonstrates one or more of a decrease in the number of bowel movements per day, a decrease in the number of watery bowel movements per day, a improvement in the daily abdominal score for pain or discomfort, an improvement in the score for daily stool consistency, a decrease in stool consistency score (from watery to formed), a decrease in the number of days per week that subjects experienced urgency, a decrease in the number of days per week that subjects experienced fecal incontinence, or a decrease in the unscheduled visit for a significant worsening of diarrhea.

In one embodiment, a subject is considered treated if the subject demonstrates an improvement in the score for daily stool consistency.

In one embodiment, a subject is considered treated if the subject demonstrates a decrease in stool consistency.

In one embodiment, a subject is considered treated if the subject demonstrates a decrease in the number of watery bowel movements per day.

In one embodiment, subject is considered treated if the subject demonstrates a decrease in the number of bowel movements per day.

In one embodiment, symptoms increased or decreased are measured from a baseline.

In one embodiment, the administering is for about 5 months. In another embodiment, the administering is for about 6 months.

In one embodiment, the administering is about 5 months or longer. In another embodiment, the administering is about 6 months or longer.

In one embodiment, the administering is for the duration of the HIV infection.

In one embodiment, the response to treatment increases after the crofelemer has been administered for longer than 4 months.

Other embodiments are disclosed infra.

DESCRIPTION OF THE FIGURES

FIG. 3 depicts a subgroup analysis showing the treatment difference in percentage of responders (crofelemer 125 mg BID vs. placebo) with associated confidence intervals and p-values.

DETAILED DESCRIPTION

Figure 1:
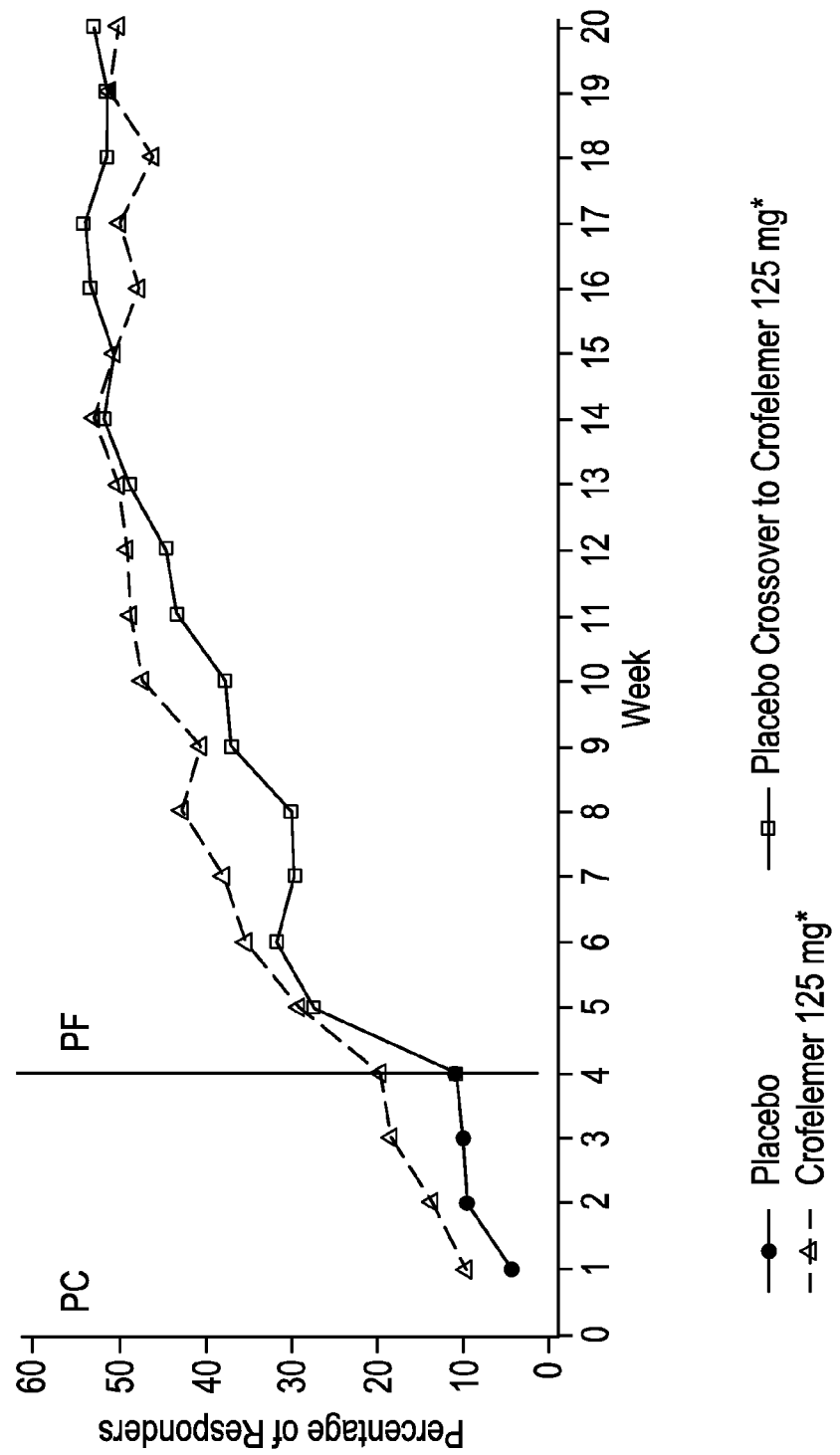
FIG. 1 shows subjects with clinical response in the crossover to placebo-free phase of the safety population.

The methods disclosed herein involved the administration of effective amounts of a proanthocyanidin polymer, e.g., crofelemer, to subjects having, for example, HIV associated diarrhea or highly active antiretroviral therapy (HAART) associated diarrhea.

Proanthocyanidins are a group of condensed tannins. Crude extracts from medicinal plants, for example, *Pycanthus angolenis* and *Baphia nitida*, have been shown to have antidiarrheal qualities in animal tests (Onwukaeme and Anuforo, 1993, Discovery and Innovation, 5:317; Onwukaeme and Lot, 1991, Phytotherapy Res., 5:254). Crude extracts which contain tannins, in particular extracts from carob pods and sweet chestnut wood, have been proposed as treatments or prophylactics (U.S. Pat. No. 5,043,160; European Patent No. 481,396).

Proanthocyanidins are comprised of at least two or more monomer units that may be of the same or different monomeric structure. The monomer units (generally termed "leucoanthocyanidin") are generally monomeric flavonoids which include catechins, epicatechins, gallocatechins, galloepicatechins, flavanols, flavonols, and flavan-3,4-diols, leucocyanidins and anthocyanidins. Therefore, the polymer chains are based on different structural units, which create a wide variation of polymeric proanthocyanidins and a large number of possible isomers (Hemingway et al., 1982, J. C. S. Perkin, 1:1217). Larger polymers of the flavonoid 3-ol units are predominant in most plants, and are found with average molecular weights above 2,000 daltons, containing 6 or more units (Newman et al., 1987, Mag. Res. Chem., 25:118).

Proanthocyanidin polymers are found in a wide variety of plants, particularly those with a woody habit of growth (e.g., *Croton* spp. and *Calophyllum* spp.). A number of different *Croton* tree species, including *Croton sakutaris, Croton gossypifolius, Croton palanostima, Croton lechleri, Croton erythrochilus* and *Croton draconoides*, found in South America, produce a red viscous latex sap called Sangre de Drago or "Dragon's Blood". U.S. Pat. No. 5,211,944 first described the isolation of an aqueous soluble proanthocyanidin polymer composition from *Croton* spp. and the use of the composition as an antiviral agent (See also Ubillas et al., 1994, Phytomedicine, 1:77). The proanthocyanidin polymer composition was shown to have antiviral activity against a variety of viruses including, respiratory syncytial, influenza, parainfluenza and herpes viruses. U.S. Pat. No. 5,211,944 also discloses the isolation of an aqueous soluble proanthocyanidin polymer composition from *Calophyllum inophylum* and the use of this composition as an antiviral agent.

Exemplary proanthocyanidin polymer compositions useful in the methods presented herein are preferably isolated from a *Croton* spp. or *Calophyllum* spp. by any method known in the art. For example, the proanthocyanidin polymer composition may be isolated from a *Croton* spp. or *Calophyllum* spp. by the method disclosed in U.S. Pat. No. 5,211,944 or in Ubillas et al., 1994, Phytomedicine 1: 77-106.

Proanthocyanidin polymer compositions useful in the methods presented herein may also be made in vitro using synthetic techniques.

In one specific embodiment, a proanthocyanidin polymer composition useful in the methods presented herein is crofelemer.

Crofelemer is an oligomeric proanthocyanidin extracted and purified from the red, viscous latex of the plant *Croton lechleri* of the family Euphorbiace. The plant is widely distributed throughout tropical Central America and South America and is widely recognized by ethnobotanists and local healers for its medicinal properties (McRae 1988), including for the treatment of diarrhea. Crofelemer is believed to exert its anti-diarrhea effect through luminal blockade of CFTR (cystic fibrosis transmembrane conductance regulator) chloride (Cl−) channel. Crofelemer has demonstrated in vitro activity against cholera toxin, forskolin, *E. coli* LT and STa toxin-mediated Cl− secretion, and to normalize electrolyte and fluid accumulation in CT-treated mice (Gabriel 1999, Fischer 2004, Adam 2005) via its effects on the CFTR channel. Crofelemer also significantly improved the secretory diarrhea in humans due to enterotoxigenic *E. coli* (DiCesare 2002), which is also thought to evoke secretory diarrhea through activation of CFTR (Kunzelmann 2002). Blockade of the CFTR channel could be anticipated to have negative consequences in man, even mimicking cystic fibrosis. However, crofelemer has virtually no systemic bioavailability in humans. When studied, the results indicated that there was little or no absorption of crofelemer from the GI tract, and that crofelemer was well tolerated by normal male subjects. Thus, the site of action of crofelemer is topical in the gastrointestinal tract.

Crofelemer (CAS 148465-45-6) is an oligomeric proanthocyanidin of varying chain lengths derived from the Dragon's Blood *Croton lecheri* of the family Euphorbiaceae. Crofelemer has an average molecular weight of between approximately 1500 daltons and approximately 2900 daltons. The monomers comprising crofelemer comprise catechin, epicatechin, gallocatechin, and epigallocatechin. The chain length of crofelemer ranges from about 3 to about 30 units with an average chain length of about 8 units. The structure of crofelemer is shown below.

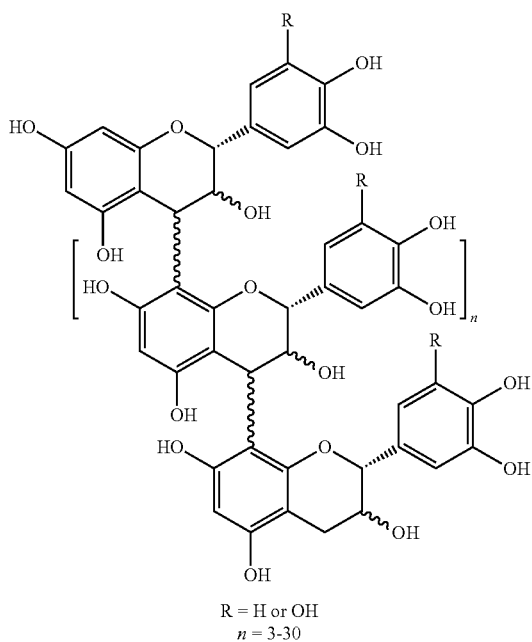

R = H or OH
n = 3-30

Wherein the average n=6.

Another method for isolating crofelemer can be found in U.S. Patent Publication No. 2005/0019389, the contents of which are expressly incorporated herein.

In other embodiments, a raw latex obtained from a *Croton* species or a *Calophyllum* species or an extract obtained from a *Croton* species or a *Calophyllum* species are useful in the methods presented herein. Exemplary extracts are described in Persinos et al., 1979, J. Pharma. Sci. 68:124 and Sethi, 1977, Canadian J. Pharm. Sci. 12:7.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with crofelemer, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement. Amelioration may be transient, prolonged or permanent or it may be variable at relevant times during or after crofelemer is administered to a subject or is used in an assay or other method described herein or a cited reference, e.g., within timeframes described infra, or about 1 hour after the administration or use of crofelemer to about 7 days, 2 weeks, 28 days, or 1, 3, 6, 9 months or more after a subject(s) has received such treatment.

The "modulation" of, e.g., a symptom, level or biological activity of a molecule, or the like, refers, for example, that the symptom or activity, or the like is detectably increased or decreased. Such increase or decrease may be observed in treated subjects as compared to subjects not treated with crofelemer, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively. Modulation may be transient, prolonged or permanent or it may be variable at relevant times during or after crofelemer is administered to a subject or is used in an assay or other method described herein or a cited reference, e.g., within times descried infra, or about 1 hour of the administration or use of crofelemer to about 2 weeks, 28 days, 3, 6, 9 months or more after a subject(s) has received crofelemer.

The language "a prophylactically effective amount" of a compound refers to an amount of crofelemer which is effective, upon single or multiple dose administration to the subject, in preventing or treating diarrhea, e.g., HIV-associated diarrhea.

As used herein, "subject" includes organisms which are capable of suffering from HIV associated diarrhea or HAART associated diarrhea or who could otherwise benefit from the administration of crofelemer as described herein, such as humans and non-human animals. The term "non-human animals" includes all vertebrates, e.g., mammals such as non-human primates, other mammals, e.g., rodents, and sheep, dog, and cow, at risk for HIV associated diarrhea or HAART associated diarrhea. A subject at risk for HIV associated diarrhea or HAART associated diarrhea is meant to include a subject at risk of developing or contracting an HIV infection.

The language "a prophylactically effective amount" of a compound refers to an amount of crofelemer which is effective, upon single or multiple dose administration to the subject, in preventing or treating the diarrhea.

The term "administration" or "administering" includes routes of introducing crofelemer to a subject to perform their intended function. Examples of routes of administration that may be used include injection, oral, inhalation, vaginal, rectal and transdermal. The pharmaceutical preparations may be given by forms suitable for each administration route. For example, these preparations are administered in tablet or capsule form, by injection, inhalation, ointment, or suppository. Administration may also be by injection, infusion or inhalation; topical by lotion or ointment; and rectal by suppositories. Oral administration is preferred. Depending on the route of administration, crofelemer can be coated with or disposed in a selected material to protect it from natural conditions that may detrimentally affect its ability to perform its intended function. Crofelemer can be administered alone, or in conjunction with either another agent or agents as described above or with a pharmaceutically-acceptable carrier, or both. Exemplary enteric coated forms of crofelemer are described in, for example, U.S. Pat. No. 7,556,831.

Administration "in combination with" one or more further therapeutic agents includes simultaneous (concurrent) and consecutive administration in any order.

As will be readily apparent to one skilled in the art, the useful in vivo dosage to be administered and the particular mode of administration may vary depending upon the age, weight and mammalian species treated, the particular compounds employed, and/or the specific use for which these compounds are employed. The determination of effective dosage levels, that is the dosage levels necessary to achieve the desired result, can be accomplished by one skilled in the art using routine pharmacological methods and in consultation with the data presented herein. In regard to crofelemer, it may be advantageous to administer 125 mg crofelemer two times per day to treat watery diarrhea if fewer watery stools are desired over a week. It is also advantageous to treat with 500 mg two times per day if an improvement in stool consistency is desired.

The term "obtaining" as in "obtaining crofelemer" is intended to include purchasing, synthesizing, isolating, extracting or otherwise acquiring crofelemer.

The language "a prophylactically effective amount" of a compound refers to an amount of crofelemer which is effective, upon single or multiple dose administration to the subject, in preventing or treating an indication. In one embodiment, the indication is HIV-associated diarrhea.

Methods of Treatment

Provided herein are methods of treating, preventing, or alleviating diarrhea or the symptoms caused by HIV infection or HAART therapy for HIV infection comprising administering to a subject in need thereof an effective amount of crofelemer. Exemplary diarrhea that can be treated or prevented using the methods presented herein include HIV associated diarrhea or highly active antiretroviral therapy (HAART) associated diarrhea.

In one embodiment, treating HIV-associated diarrhea includes an improvement of the following symptoms of HIV associated diarrhea or HAART associated diarrhea, including, for example, a decrease in the number of bowel movements per day (frequency), a decrease in the number of watery bowel movements per day, a decrease in symptom frequency (urgency, fecal incontinence), a decrease in symptom severity (abdominal pain or discomfort), a decrease in daily stool consistency score (watery to formed), or a decrease in stool consistency leading to formed stools from watery stools.

In one specific embodiment, treatment is defined as two or less watery bowel movements per week. More specifically, treatment is defined as two or less watery bowel movements per week during at least two of the four weeks of treatment with crofelemer.

In other specific embodiments, treatment can also include, for example, one or more of a decrease in the number of bowel movements per day, a decrease in the number of watery bowel movements per day, a improvement in the daily abdominal score for pain or discomfort, an improvement in the score for daily stool consistency, a decrease in the number of days per week that subjects experienced urgency, a decrease in the number of days per week that subjects experienced fecal incontinence, or a decrease in the unscheduled visit for a significant worsening of diarrhea.

In one aspect, provided herein are methods of treating HIV associated diarrhea or highly active antiretroviral therapy (HAART) associated diarrhea in an HIV positive subject. Treatment of the diarrhea can include, for example, one or more of a decrease in the number of bowel movements per day, a decrease in the number of watery bowel movements per day, a improvement in the daily abdominal score for pain or discomfort, an improvement in the score for daily stool consistency, a decrease in stool consistency, a decrease in the number of days per week that subjects experienced urgency, a decrease in the number of days per week that subjects experienced fecal incontinence, or a decrease in the unscheduled visit for a significant worsening of diarrhea.

In one aspect, provided herein are methods of treating stool consistency in an HIV positive subject, wherein a subject is considered treated if there is an improvement in the score for daily stool consistency and/or a decrease in stool consistency score a measured throughout the day or days or weeks. This decrease may be measured from a baseline. The baseline may be determined in the days to week prior to treatment with crofelemer. Treatment comprises administering about 250 mg to about 1000 mg per day; administering about 250 mg per day; administering 1000 mg per day; administering about 125 mg two times per day; or administering about 500 mg two times per day of crofelemer to a subject in need thereof.

In one aspect, provided herein are methods of improving stool consistency in an HIV positive subject wherein a subject is considered treated if there is an improvement in stool consistency and/or a decrease in stool consistency throughout the day or days or weeks. This increase may be measured from a baseline. The baseline may be determined in the days to week prior to treatment with crofelemer. Treatment comprises administering about 250 mg to about 1000 mg per day; administering about 250 mg per day; administering 1000 mg per day; administering about 125 mg two times per day; or administering about 500 mg two times per day of crofelemer to a subject in need thereof.

In one aspect, provided herein are methods of alleviating watery diarrhea in an HIV positive subject, wherein a subject is considered treated if the subject experiences a decrease in the number of watery bowel movements per day and/or over days, a week or weeks of administration of crofelemer. This decrease may be measured from a baseline. The baseline may be determined in the days to week prior to treatment with crofelemer. Treatment comprises administering about 250 mg to about 1000 mg per day; administering about 250 mg per day; administering 1000 mg per day; administering about 125 mg two times per day; or administering about 500 mg two times per day of crofelemer to a subject in need thereof.

In one aspect, presented herein are methods a decreasing the number of bowel movements per day, wherein a subject is considered treated if there is a decrease in the number of bowel movements per day as measured from a baseline. The baseline may be determined in the days to week prior to treatment with crofelemer. Treatment comprises administering about 250 mg to about 1000 mg per day; administering about 250 mg per day; administering 1000 mg per day; administering about 125 mg two times per day; or administering about 500 mg two times per day of crofelemer to a subject in need thereof.

Crofelemer may be administered, for example, once a day, twice a day, three times a day, or four times or more often as necessary per day. Crofelemer may be administered in doses, for example of from about between 25 mg BID to about 3000 mg TID, preferably crofelemer is administered from between about 125 mg to about 1000 mg per day. In another embodiment, crofelemer is administered between 125 mg BID to about 500 mg BID depending of symptoms. In another embodiment, crofelemer is administered as 125 mg BID. In another embodiment, crofelemer is administered as 500 mg BID. Crofelemer may be administered orally, for example, in tablet form, powered form, liquid form or in capsules.

In exemplary embodiments, the subject is administered 250, 500, or 1000 mg/day of crofelemer.

In specific embodiments, the subject is administered 125, 250 or 500 mg p.o. b.i.d (orally twice per day). Other appropriate dosages for methods may be determined by health care professionals or by the subject. The amount of crofelemer administered daily may be increased or decreased based on the weight, age, health, sex or medical condition of the subject. One of skill in the art would be able to determine the proper dose for a subject based on this disclosure and the data presented in the Examples, which follow.

In other embodiments, the subject is treated with crofelemer for 2, 4, 6, 8, 10, 12, 14, 16, 18, 20, 22, 24 or more weeks or 26 or more weeks. In one embodiment, the subject is administered crofelemer for the duration of the disease. Length of treatment may vary depending on the type and length of disease and the proper length of treatment may be easily determined by one of skill in the art having the benefit of this disclosure. Treatment may be prior to infection, during infection, or after suspected infection and for a period of time suggested by a medical professional to reduce or eliminate diarrhea.

Subjects in need thereof include subjects having or that are susceptible to or who have HIV-associated diarrhea or HAART associated diarrhea.

As used herein, a therapeutically effective amount means an amount effective, when administered to a human or non-human subject, to provide a therapeutic benefit such as an amelioration of symptoms, e.g., an amount effective to decrease the symptoms HIV-associated diarrhea.

According to certain embodiments, crofelemer may be administered in combination with other compounds, including for example, anti-diarrheal agents or anti-HIV agents, including, for example, anti-retroviral agents.

According to one aspect, provided herein are methods of treating HIV associated diarrhea or highly active antiretroviral therapy (HAART) associated diarrhea in an HIV positive subject that has previously used protease inhibitors, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer to a male subject in need thereof. As used herein, "previously used" includes, for example, subjects who have used protease inhibitors (PIs) prior to crofelemer therapy or overlapping with crofelemer therapy, but the PI use began prior to the first dose of crofelemer therapy.

Pharmaceutical Preparations

Also provided herein are pharmaceutical compositions, comprising an effective amount of a crofelemer described herein and a pharmaceutically acceptable carrier. In a further embodiment, the effective amount is effective to treat HIV-associated diarrhea and/or HAART associated diarrhea.

Examples of the preparation and use of crofelemer have been described in U.S. Pat. No. 7,556,831, US Patent Publication 20070254050 and US Patent Publication 20080031984, all of which are incorporated herein by reference in their entirety.

One embodiment includes pharmaceutical compositions comprising crofelemer and a pharmaceutically acceptable carrier.

The pharmaceutical compositions described herein may further comprise excipients, for example, one or more of a diluting agent, binding agent, lubricating agent, disintegrating agent, coloring agent, flavoring agent or sweetening agent. Compositions may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In certain embodiments, these pharmaceutical compositions are suitable for topical or oral administration to a subject. In other embodiments, as described in detail below, the pharmaceutical compositions may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to crofelemer as described herein, compositions containing crofelemer, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing crofelemer include those suitable for oral, nasal, topical (including buccal and sublingual), rectal, vaginal, aerosol and/or parenteral administration. The compositions may conveniently be presented in unit dosage form and may be prepared by any methods known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.01% to about 99% of active ingredient, for example, from about 5% to about 70%, or from about 10% to about 30%.

Liquid dosage forms for oral or rectal administration of crofelemer may include, for example, pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to crofelemer may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Dosage forms for the topical or transdermal administration of crofelemer can include, for example, powders, sprays, ointments, pastes, creams, lotions, gels, solutions, patches and inhalants. The ointments, pastes, creams and gels may contain, in addition to crofelemer, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a croflemer, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Examples of suitable aqueous and non-aqueous carriers which may be employed in the pharmaceutical compositions can include, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In one embodiment, crofelemer is enteric coated so as to protect it from degradation by the acidic conditions of the stomach and/or from interactions with proteins, such as pepsin, present in the stomach, e.g., an enteric protected formulation. In a specific embodiment, crofelemer is in tablet form. In yet another embodiment, the tablet is enteric coated, e.g., Eudragit®. In one embodiment, crofelemer is formulated as an enteric coated bead or granule in an enteric coated capsule shell. In another embodiment, crofelemer is formulated in a delayed release composition.

In certain embodiments, the composition is formulated with a compound or compounds which neutralize stomach acid. Alternatively, the pharmaceutical composition containing the composition is administered either concurrent with or subsequent to or after administration of a pharmaceutical composition which neutralize stomach acid. Compounds, such as antacids, which are useful for neutralizing stomach acid include, but are not limited to, aluminum carbonate, aluminum hydroxide, bismuth subnitrate, bismuth subsalicylate, calcium carbonate, dihydroxyaluminum sodium carbonate, magaldrate, magnesium carbonate, magnesium hydroxide, magnesium oxide, and mixtures thereof. Compounds that are able to reduce the secretion of stomach acid and/or are able to reduce the acidity of stomach fluid are well known in the art and include, but are not limited to, antacids (aluminum hydroxide, aluminum carbonate, aluminum glycinate, magnesium oxide, magnesium hydroxide, magnesium carbonate, calcium carbonate, sodium bicarbonate), stomach acid blockers and a combination of any of the foregoing. In general, any drug that has been approved for sale by the relevant government agency and is able to reduce the production of stomach acid and/or reduce the acidity of stomach fluid can be administered in combination with an inhibitor molecule, such as crofelemer, in accordance with the methods presented herein.

In a particular embodiment where crofelemer is not enteric coated, crofelemer is formulated with one or more compounds that are able to reduce the secretion of stomach acid and/or able to reduce the acidity of stomach fluid. In an exemplary embodiment, crofelemer is formulated in a controlled release (delayed release) composition, such as Merck GEM, Alza OROS, wax matrix (release is primarily delayed until after the formulation passes out of the stomach and into the intestine).

Also provided herein are pharmaceutical formulations of crofelemer comprising the composition along with a pharmaceutically acceptable vehicle, at a dose which is therapeutically effective at treating HIV associated diarrhea or HAART associated diarrhea. In one embodiment, a directly compressible crofelemer (e.g., that can be directly compressed, without excipients, into a tablet of pharmaceutically acceptable hardness and friability) compressed into a tablet, optionally with a lubricant, such as but not limited to magnesium stearate, is enteric coated. These formulations can be prepared by methods known in the art, see, e.g. methods described in Remington's Pharmaceutical Sciences, 18th Ed., ed. Alfonso R. Gennaro, Mack Publishing Co., Easton, Pa., 1990.

In a specific embodiment, the proanthocyanidin polymer composition comprises crofelemer (CAS 148465-45-6).

In a more another embodiment, a composition is enteric coated. Enteric coatings are those coatings that remain intact in the stomach, but will dissolve and release the contents of the dosage form once it reaches the small intestine. A large number of enteric coatings are prepared with ingredients that have acidic groups such that, at the very low pH present in the stomach, i.e. pH 1.5 to 2.5, the acidic groups are not ionized and the coating remains in an undissociated, insoluble form. At higher pH levels, such as in the environment of the intestine, the enteric coating is converted to an ionized form, which can be dissolved to release the inhibitor molecule. Other enteric coatings remain intact until they are degraded by enzymes in the small intestine, and others break apart after a defined exposure to moisture, such that the coatings remain intact until after passage into the small intestines.

Polymers which are useful for the preparation of enteric coatings include, but are not limited to, shellac, starch and amylose acetate phthalates, styrene-maleic acid copolymers, cellulose acetate succinate, cellulose acetate phthalate (CAP), polyvinylacetate phthalate (PVAP), hydroxypropylmethylcellulose phthalate (grades HP-50 and HP-55), ethylcellulose, fats, butyl stearate, and methacrylic acid-methacrylic acid ester copolymers with acid ionizable groups. In one embodiment, the pharmaceutical composition contains a polymeric proanthocyanidin composition and the enteric coating polymer Eudragit®. L 30D, an anionic copolymer of methacrylic acid and methyl acrylate with a mean molecular weight of 250,000 Daltons. In another embodiment, the enteric coating polymer is Eudragit®. L 30D-55. Application of the enteric coating to the crofelemer composition can be accomplished by any method known in the art for applying enteric coatings. For example, but not by way of limitation, the enteric polymers can be applied using organic solvent based solutions containing from 5 to 10% w/w polymer for spray applications and up to 30% w/w polymer for pan coatings. Solvents that are commonly in use include, but are not limited to, acetone, acetone/ethyl acetate mixtures, methylene chloride/methanol mixtures, and tertiary mixtures containing these solvents. Some enteric polymers, such as methacrylic acid-methacrylic acid ester copolymers can be applied using water as a dispersant. The volatility of the solvent system must be tailored to prevent sticking due to tackiness and to prevent high porosity of the coating due to premature spray drying or precipitation of the polymer as the solvent evaporates.

In another embodiment, the pharmaceutical composition comprising crofelemer is formulated as enteric coated granules or powder (microspheres with a diameter of 300-5001) provided in either hard shell gelatin capsules or suspended in an oral solution for pediatric administration. The enteric coated powder or granules may also be mixed with food, particularly for pediatric administration.

The granules and powder can be prepared using any method known in the art, such as but not limited to, crystallization, spray-drying or any method of comminution, for example, using a high speed mixer/granulator. Exemplary formulations may be found, for example, in the following US patents and applications U.S. Pat. No. 7,341,744; U.S. Ser. No. 11/510,152; and U.S. Ser. No. 12/175,131.

Regardless of the route of administration selected, crofelemer is formulated into pharmaceutically-acceptable dosage forms by methods known to those of skill in the art.

In combination therapy treatment, both the compounds and the other drug agent(s) are administered to mammals (e.g., humans, male or female) by methods known in the art. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment in which another therapeutic agent is administered to an animal, the effective amount of the compound is less than its effective amount in case the other therapeutic agent is not administered. In another embodiment, the effective amount of the agent is less than its effective amount in case the compound is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one or more embodiments, two or more therapies are administered within the same patient's visit.

Kits

Kits are also provided herein, for example, kits for treating a diarrhea, e.g., HIV-associated diarrhea in a subject. The kits may contain, for example, crofelemer or a pharmaceutical composition comprising crofelemer and instructions for use. The instructions for use may contain prescribing information, dosage information, storage information, and the like.

Label instructions include, for example, instructions to take the crofelemer for at least 3 days for the treatment of HIV associated or HAART associated diarrhea. The instructions could also read, for example, take from between 125 mg BID to 500 mg BID of crofelemer until resolution of symptoms or for 24 weeks for treatment or HIV-associated diarrhea. The instructions could also read, for example, take 125 mg BID of crofelemer until resolution of symptoms or for 24 weeks for treatment or HIV-associated diarrhea. The instructions could also read, for example, take 500 mg BID of crofelemer until resolution of symptoms or for 24 weeks for treatment or HIV-associated diarrhea.

Label instructions may further or alternately include, for example, instructions to take the crofelemer from between 125 mg BID to 500 mg BID of crofelemer until resolution of symptoms or for 26 weeks for treatment or HIV-associated diarrhea. The instructions could also read, for example, take 125 mg BID of crofelemer until resolution of symptoms or for 26 weeks for treatment or HIV-associated diarrhea. The instructions could also read, for example, take 250 mg BID of crofelemer until resolution of symptoms or for 26 weeks for treatment or HIV-associated diarrhea. The instructions could also read, for example, take 500 mg BID of crofelemer until resolution of symptoms or for 26 weeks for treatment or HIV-associated diarrhea.

EXAMPLES

It should be appreciated that the invention should not be construed to be limited to the example, which is now described; rather, the invention should be construed to include any and all applications provided herein and all equivalent variations within the skill of the ordinary artisan.

Example 1

Pulmonary Effects of Orally Administered Crofelemer in Rats

Three treatment groups of eight male rats were administered Crofelemer at respective dose levels of 60, 200, and 600 mg/kg. An additional group of eight male rats served as control animals and were administered the vehicle, purified water. Crofelemer and vehicle were administered at a dose volume of 10 mL/kg. One additional group of eight male rats received the positive control article, baclofen, at a dose level of 100 mg/kg and a dose volume of 15 mL/kg. Crofelemer, positive control article, and vehicle were administered to all groups via oral gavage.

Observations for mortality, morbidity, injury, and the availability of food and water were conducted at least twice daily for all animals. Clinical observations were conducted prior to dosing, approximately 1 hour postdose, and following completion of the pulmonary monitoring periods (approximately 4 hours postdose). Body weights were measured and recorded prior to dosing (Day 1). Pulmonary function (respiratory rate, tidal volume, and minute volume) was monitored for approximately 1 hour prior to dosing to establish baseline and for approximately 4 hours postdose. Following the pulmonary monitoring periods, all animals were euthanized and the carcasses were discarded without further evaluation.

Crofelemer, administered orally to male rats at doses of 60, 200, and 600 mg/kg did not produce any effects on mortality or any of the quantitative respiratory endpoints over the course of the study. With respect to the basic respiratory endpoints evaluated in this study, oral administration of Crofelemer produced no adverse effects in rats at doses up to and including 60 mg/kg.

Example 2

13-Week Oral Toxicity Study of Crofelemer Administered to Mice

Three treatment groups of 15 male and 15 female mice were administered Crofelemer at respective dose levels of 40, 400, and 1200 mg/kg/day. One additional group of 15 animals/sex served as the control and received the vehicle, purified water. The vehicle or Crofelemer was administered to all groups at a dose volume of 10 mL/kg. Additionally, four groups of eight or 39 animals/sex/group served as toxicokinetic (TK) animals and received the control or Crofelemer in the same manner as the main study groups at respective dose levels of 0, 40, 400, or 1200 mg/kg/day. Due to mortalities, the main study and TK animals at 1200 mg/kg/day were administered Crofelemer for up to 55 or 56 days, respectively.

Observations for morbidity, mortality, injury, and the availability of food and water were conducted twice daily for all animals. Detailed clinical observations for clinical signs were conducted weekly on all main study animals. Body weights were measured and recorded weekly on all animals. Food consumption was measured and recorded weekly on all main study animals. Ophthalmoscopic examinations were conducted pretest and prior to necropsy for all main study animals. Blood samples for clinical pathology evaluations were collected from main study animals in extremis and at termination. Blood samples for determination of the plasma concentrations of Crofelemer were collected from designated TK animals at designated time points on Days 1, 56, and 91. After blood collection, the TK animals were euthanized and the carcasses were discarded, with the exception of designated animals at 1200 mg/kg/day. The toxicokinetic parameters were determined for Crofelemer from concentration time data in the test species. At study termination, necropsy examinations were performed and organ weights were recorded for all main study animals and designated TK animals at 1200 mg/kg/day. Tissues were microscopically examined for main study animals at 0, 400, and 1200 mg/kg/day. Beginning on Day 7, a limited gross necropsy examination was performed on any TK animal euthanized in extremis or found dead in an effort to determine the cause of death. Tissues were collected and preserved for possible future examination from main study animals at 40 mg/kg/day and designated TK animals at 1200 mg/kg/day.

Twice-daily oral gavage administration of Crofelemer at 0, 40, or 400 mg/kg/day for 13 weeks or 1200 mg/kg/day for 8 weeks in mice was only tolerated in females at 40 mg/kg/day. Crofelemer-related mortalities were evident in a single male at 40 mg/kg/day and in both sexes at 400 and 1200 mg/kg/day. Crofelemer-related body weight effects were evident at ≥400 mg/kg/day in both sexes, and food consumption effects were evident at 40 mg/kg/day in females and ≥400 mg/kg/day in both sexes. Clinical pathology, organ weight, and macroscopic effects were observed in both sexes at 1200 mg/kg/day. Due to mortality at 40 mg/kg/day, there was no No-Observed-Adverse-Effect-Level (NOAEL) in males; however, the NOAEL was determined to be 40 mg/kg/day in females.

Example 3

Neurobehavioral Evaluation of Orally Administered Crofelemer in Rats

Three treatment groups of six male rats were administered Crofelemer at respective dose levels of 60, 200, and 600 mg/kg. One additional group of six male rats served as the control and received the vehicle, purified water. Another additional group of six male rats received the positive control article, chlorpromazine hydrochloride, at a dose level of 20 mg/kg. Crofelemer, positive control article, or vehicle was administered to all groups once via oral gavage at a dose volume of 10 mL/kg.

Observations for morbidity, mortality, injury, and the availability of food and water were conducted at least twice daily for all animals. Clinical observations were conducted following each functional observational battery (FOB) examination. FOB evaluations were conducted predose and at approximately 1 and 24 hours postdose. Body weights were measured and recorded prior to dosing on Day 1. At study termination, all animals were euthanized and the carcasses were discarded without further evaluation.

Crofelemer administered orally to male rats at doses of 60, 200, and 600 mg/kg did not produce any effects on mortality, clinical observations, body weight, or any of the neurobehavioral measures tested. Therefore, with respect to the basic neurobehavioral endpoints evaluated in this study, oral administration of Crofelemer produced no effects in rats at doses up to and including 600 mg/kg.

Example 4

Effects of Orally Administered Crofelemer on Gut Motility Function in the Rat Three treatment groups of eight male rats were administered Crofelemer at respective dose levels of 60, 200, and 600 mg/kg. One additional group of eight male rats received the positive control article, morphine, at a dose level of 20 mg/kg. An additional group of eight male rats served as the control and received the vehicle, purified water. The vehicle, positive control article, or Crofelemer was administered to all groups via oral gavage once on Day 1 of the study at a dose volume of 10 mL/kg. Approximately 1 hour after administration, the test meal, 5% charcoal suspension in 10% *Acacia* in deionized water, was administered to all animals via oral gavage at a dose volume of 10 mL/kg.

Observations for morbidity, mortality, injury, and the availability of food (except during fasting periods) and water were conducted at least twice daily for all animals. Clinical observations were conducted prior to dosing, and prior to termination. Body weights were measured and recorded prior to dosing on Day 1. Approximately 30 minutes following test meal administration all animals were euthanized, the small intestine was surgically removed, and the total intestine length and the distance the charcoal traveled were both measured. The carcasses were discarded without further evaluation.

Crofelemer, administered orally to male rats at doses of 60, 200, or 600 mg/kg did not produce mortality or any clinical observations. Crofelemer-related, dose-dependent decreases in gastrointestinal propulsion were noted in all Crofelemer-treated groups; however, statistically significant decreases were only noted following the 200 and 600 mg/kg doses. Due to low recovery values, the dose levels actually administered to the animals in the 60 and 200 mg/kg groups were 51 and 169 mg/kg, respectively.

Example 5

Cardiovascular Effects of Orally Administered Crofelemer in the Beagle Dog

The same four male beagle dogs were administered the control article, placebo tablets in gelatin number 12 Torpac lock ring gelatin capsules (0 mg/kg), and Crofelemer at dose levels of approximately 60, 200, and 600 mg/kg according to a modified Latin square design, with one animal/sex/treatment dosing each week followed by at least a 7 day washout period between administrations, until each animal received all treatments. The control article and Crofelemer were administered to all animals orally via gelatin capsule.

The animals were previously surgically instrumented with radio transmitters for measurement of body temperature, blood pressure, heart rate, and the electrocardiogram (ECG). Body temperature, systolic, diastolic, and mean arterial blood pressures, heart rate, and ECG parameters (QRS duration and the RR, PR, and QT intervals) were monitored continuously from at least 2 hours prior to dosing until at least 20 hours postdose. Nine days prior to the first administration, untreated animals were continuously monitored for cardiovascular endpoints for at least 22 hours. These data were used in the calculation of the corrected QT interval throughout the study.

Observations for morbidity, mortality, injury, and the availability of food and water were conducted at least twice daily for all animals. Clinical observations were conducted prior to dosing and following completion of the cardiovascular monitoring period. Body weights were measured and recorded on the day prior to each administration. At study termination, the animals were transferred to the stock colony.

Crofelemer administered orally to male dogs at doses of 60, 200, and 600 mg/kg did not produce mortality nor any effects on the ECG over the course of the study. Following doses of 200 and 600 mg/kg the test article produced clinical observations of red, black, or brown feces; soft, watery, and/or mucoid feces; and/or black or brown material below the cage (fecal material). Therefore, with respect to all the physiological parameters evaluated as a part of this cardiovascular study, a no-observable-adverse-effect-level (NOAEL) of 600 mg/kg has been established.

Example 6

Effects of Crofelemer on Herg K+ Currents in Hek-293 Cells

The hERG channel was stably expressed in a subclone (HEK-293/hERG) of the HEK-293 cell line. The effect of Crofelemer was measured on the maximum amplitude of the tail current. This parameter was determined from current traces obtained from voltage-clamped HEK-293/hERG cells, using patch-clamp techniques in the whole cell configuration.

Crofelemer was tested at 5 concentrations for the first set of experiments: 0.001 µM, 0.01 µM, 0.1 µM, 1.0 µM, and 10.0 µM and 6 concentrations for the second set of experiments: 0.1 µM, 0.3 µM, 1 µM, 3 µM, 10 µM, and 30 µM. Positive control article was tested at 10 µM. Negative control article was deionized water.

Crofelemer inhibited hERG tail current in a dose-dependent manner. The estimated IC50 values were 1.79 µM for the first set of experiments and 1.75 µM for the second set of experiments. Cisapride (positive control, 10 µM) inhibited hERG tail current by an average of 99.67% and 100.47% for the first and second sets of experiments respectively, which is consistent with its known pharmacological action.

Example 7

Effects of Food on the PK of Crofelemer 500 mg

A total of 28 subjects were to be enrolled into this study. Subjects were randomized on Day 1 at a 1:1 ratio to Group 1 (fasted then fed) or Group 2 (fed then fasted). Randomization was stratified by sex. Each subject received a single dose of crofelemer 500 mg (administered orally as 2×250 mg tablets) with a high fat meal (crofelemer fed) and after fasting (crofelemer fasted). The fasted/fed study periods were separated by 7 days. The sequence of fasted/fed or fed/fasted dosing on Days 1 and 8 were determined by randomization on Day 1.

Blood samples for PK analyses of crofelemer were collected pre-dose and up to 48 hours post-dose following both fasted and fed single-dose treatment administrations.

During the food effect study period, subjects fasted overnight (no food for approximately 9.5 hours) prior to administration of a high fat breakfast (crofelemer fed) or fasted overnight for 10 hours prior to administration of the single dose of study drug (crofelemer fasted).

Assessments of the treatment regimen on the relative bioavailability of crofelemer were based on comparisons of plasma concentrations of crofelemer across each study phase. Whole blood samples were drawn at the following times (actual blood collection times were recorded in the source/eCRF): Days 1 and 8: pre-dose (approximately 1 hour before dosing), and at 0.5, 1, 2, 4, 6, 8, 10, 12, 16, 24, 30, 36, 42, and 48 hours post-dose.

A pharmacokinetic/pharmacodynamic (PK/PD) analysis was intended to be performed using all subjects who had paired ECG and plasma concentrations for crofelemer. The PK/PD pharmacokinetic-pharmacodynamic analysis was not done due to insufficient pharmacokinetic PK data.

This analysis was also designed to assess the relationship between the concentration of crofelemer and QTcF. However, only 3 samples were found to have concentrations above the LLOQ of 50 ng/mL so the relationship of crofelemer concentration to QTcF could not be assessed.

The mean baseline corrected change in heart rate showed a decrease in heart rate of −1.1 bpm and −1.0 bpm for crofelemer fasting and fed, respectively, at 4 hours. The mean baseline corrected change in heart rate showed an increase in heart rate of 3.5 bpm and 1.6 bpm for crofelemer fasting and fed, respectively, at 12 hours. The heart rate changes were of no clinical significance. There were no tachycardic or bradycardic outliers on crofelemer fasting or fed.

Example 8

Efficacy and Safety of Crofelemer for the Treatment of HIV Associated Diarrhea

This study was conducted to determine if treatment with Crofelemer 125 mg, 250 mg and 500 mg orally (p.o.) twice daily improves the frequency, consistency, and urgency of bowel movements in subjects with HIV-associated diarrhea compared to placebo. Male or female subjects aged ≥18 years, with HIV-1 infection confirmed by standard serological tests and/or viral load and history of diarrhea of at least 1 month duration.

The study was a randomized, double-blind, parallel-group, placebo-controlled, multicenter study. The study was done in two stages. Both stages consisted of a 10+4 day, single-blind, placebo screening phase; followed by randomization and a 31-day, double-blind, placebo-controlled treatment phase; and concluded with a 20-week placebo-free extension phase. In Stage I (dose selection stage), the double-blind phase had four arms: three doses of crofelemer (125 mg b.i.d., 250 mg b.i.d., and 500 mg b.i.d.) and placebo b.i.d. The chance of receiving crofelemer or placebo was 3:1 (1:1:1:1 ratio). Subjects on crofelemer rolling over into the extension phase remained on their same dose, or if on placebo was re-randomized to one of the three aforementioned doses. After Stage I is completed an interim analysis was conducted and the dose of crofelemer that appears to work better, be safer, and/or better tolerated than the others, was selected to use exclusively in Stage II. Stage II will have only two arms in the double blind, placebo-controlled treatment phase: the selected dose of crofelemer (crofelemer 125 mg) and placebo. The chances of receiving crofelemer or placebo will be 1:1. All subjects rolling over into the 20-week placebo-free extension phase in Stage II were assigned the previously selected dose of crofelemer. During both Stage I and Stage II, subjects will first enter a single-blind placebo screening phase lasting 10+4 days during which time bowel movement frequency, consistency, and urgency was measured. Antiretroviral therapy and therapy for associated conditions (including prophylactic antibiotics for *Pneumocystis carinii* (PCP) or infection must have remained at a constant level from four weeks prior to screening through the placebo-controlled treatment phase. Any changes in antiretroviral therapy during any point in the study must be reported to the site and documented on the subject's case report form.

The key efficacy analyses were based on the data from the 4-week efficacy assessment period of the placebo-controlled treatment phase. Analysis of the primary endpoint was based on the Intent to Treat (ITT) population and will compare the proportion of responders in the placebo group to the proportion of responders in the crofelemer 125 mg group. The primary efficacy endpoint was clinical response, defined as two or less watery bowel movements per week, during at least two of the four weeks of the 4-week efficacy assessment period in the ITT population. The secondary efficacy variables during the 4-week efficacy assessment period in the ITT population were:

The number of bowel movements per day
The number of watery bowel movements per day;
The score for daily abdominal pain or discomfort;
The score for daily stool consistency;
The number of days per week that subjects experienced urgency;
The number of days per week that subjects experienced fecal incontinence; and
Proportion of subjects undergoing an unscheduled visit for a significant worsening or clinically significant exacerbation of diarrhea during the 4-week efficacy assessment period.

This study consisted of a dose-selection stage, an interim analysis period, and a dose-assessment stage.

Stage I: Dose-Selection Stage

Subjects were randomized 1:1:1:1, at approximately 50 subjects per treatment group: crofelemer 125 mg p.o. b.i.d.; crofelemer 250 mg p.o. b.i.d.; crofelemer 500 mg p.o. b.i.d.; and placebo p.o. b.i.d.

Crofelemer 125 mg, 250 mg, and 500 mg, or matching placebo, was administered as a tablet combination orally twice daily with fluids at least one half hour before the morning and evening meals.

The double-blind, placebo-controlled treatment phase consisted of an initial 3-day run-in period (Days −3 to −1) followed by a 4-week efficacy assessment period (Days 1 to 28). The run-in period assured that the effects of study medication were established before the 4-week efficacy assessment period is commenced.

Subjects who completed the placebo-controlled treatment phase entered a 20-week placebo-free extension phase. Subjects in the Crofelemer 125 mg p.o. b.i.d., Crofelemer 250 mg p.o. b.i.d or Crofelemer 500 mg b.i.d. groups continued to receive these therapies throughout the placebo-free treatment phase; subjects who received placebo were re-randomized to receive either Crofelemer 125 mg p.o. b.i.d, Crofelemer 250 mg p.o. b.i.d. or 500 mg p.o. b.i.d (1:1:1). There was no risk of placebo during the 20-week extension phase, and subjects were permitted ad libitum (prn) use of ADM.

Stage I ended when about 50 subjects were randomized to each of the four treatment groups. Enrollment was stopped at approximately 50 subjects per treatment group until the interim analysis and decision for Stage II are completed.

Interim Analysis

An interim analysis was performed when approximately 50 subjects (actual totals in the Tables, which follow) were randomized to each of four treatment groups and completed the placebo-controlled treatment period or terminate the study (not in either case to include the 14-day post-dosing telephone call for assessment of adverse events). Based upon an assessment of efficacy and safety, subjects were select to continue one of the crofelemer doses along with placebo into Stage II.

Stage II: Dose-Assessment Stage

Once the interim analysis was completed, enrollment resumed. Subjects were screened for eligibility for randomization based on the criteria in Stage I. Subjects who enter the double-blind, placebo-controlled treatment phase in Stage II were randomized to one of two treatment groups: crofelemer 125 mg p.o. b.i.d. or placebo p.o. b.i.d.

Crofelemer 125 mg, 250 mg, and 500 mg, or matching placebo, was administered as a tablet combination orally twice daily with fluids at least one half hour before the morning and evening meals.

An objective of the dose-assessment stage was to determine the proportion of HIV-positive subjects experiencing relief of diarrhea with crofelemer 125 mg p.o. b.i.d. compared to placebo p.o. b.i.d. during the placebo-controlled treatment phase. Other objectives were to evaluate the effects of crofelemer 125 mg p.o. b.i.d. vs. placebo on:

i. Number of bowel movements per day (frequency)
ii. Number of watery bowel movements per day
iii. Symptom frequency (urgency, fecal incontinence)
iv. Symptom severity (abdominal pain or discomfort); and
v. Daily stool consistency score.

The ratio of randomization to crofelemer 125 mg p.o. b.i.d or placebo p.o. b.i.d was 1:1. Subjects who completed the double-blind treatment phase participated in the 20-week, placebo-free extension phase and received crofelemer 125 mg p.o. b.i.d. Subjects who enrolled in Stage I, and who received either crofelemer 125 mg p.o. b.i.d., 250 mg p.o. b.i.d. or 500 mg p.o. b.i.d, remained on their previously assigned dose. However, subjects were re-assigned to crofelemer 125 mg p.o. b.i.d. if, in the opinion of the investigator, the response to or tolerance to their current dose was inadequate. Treatment remained blinded during this treatment period, including the possibility that subjects were switched to the same dose they had initially been taking.

All study procedures performed in Stage I were otherwise be identical to Stage II.

Subjects randomized during Stages I and II were combined and included in sample size calculations and analysis of efficacy and safety.

The following criteria were used for collecting data to evaluate the efficacy of crofelemer on HIV-associated diarrhea.

Study Diary (IVRS) Definitions

Diarrhea, includes, frequent loose or watery bowel movements

Bowel movement is defined as a trip to the bathroom with evacuation of stool; number of bowel movements means number of trips to the bathroom with evacuation of stool.

Watery bowel movement is defined as stool that can be poured;

Loose bowel movement is defined as soft blobs with no shape or form;

Formed bowel movement is defined as a stool like a soft sausage;

Hard bowel movement is defined as a stool like a hard or lumpy sausage; and

Very hard bowel movement is defined as hard lumps or nuts that are hard to pass.

Urgency is defined as having to rush to the bathroom for a bowel movement

Fecal incontinence is defined as leaking or passing stool at unwanted times (two teaspoons or more of stool).

Abdominal pain or discomfort is defined as pain, cramping, or bloating that is uncomfortable and/or interrupts normal activities.

Stool Samples

Each sample collected was analyzed as follows:

Visit 0

*Clostridium difficile* toxin;

Enteric pathogens, O&P examination;

*Giardia*-specific antigen by EIA;

Modified acid-fast stain for *Cryptosporidium, Cyclospora*, and *Isospora;*

Lactoferrin (qualitative); and

Occult blood.

Visit 3

*Clostridium difficile* toxin;

Enteric pathogens, O&P examination;

*Giardia*-specific antigen by EIA; and

Modified acid-fast stain for *Cryptosporidium, Cyclospora*, and *Isospora.*

Visits 4, 5, 6, 7 and 8

*Clostridium difficile* toxin;

Enteric pathogens, O&P examination

*Giardia*-specific antigen by EIA

Modified acid-fast stain for *Cryptosporidium, Cyclospora*, and *Isospora*

Analysis of the Primary Efficacy Variable

The primary efficacy endpoint is clinical response; subjects are classified responders if they reported two or less watery bowel movements per week, during at least two of the four weeks of the efficacy assessment period of the placebo-controlled treatment phase.

Analysis of Secondary Efficacy Variables

For every subject, a mean baseline, a mean for Weeks 1 to 4, and change from baseline will be calculated for the following variables:

Number of bowel movements per day;

Number of watery bowel movements per day;

Daily abdominal pain or discomfort score;

Daily stool consistency score;

The number of days per week that subjects experienced urgency; and

The number of days per week that subjects experienced fecal incontinence.

Each of the secondary continuous variables will be analyzed as percent change from baseline.

The daily abdominal pain or discomfort score were assigned scores as follows: none=0, mild=1, moderate=2, severe=3, that is the greater the score the worse the pain or discomfort. Stool consistencies will be assigned scores as follows: 1=very hard, 2=hard, 3=formed, 4=loose, 5=watery for each bowel movement.

The stool consistency score was computed from the mean of these scores each day.

Table 1 below shows the baseline characteristics for the placebo-controlled treatment phase, including the diagnosed cause of diarrhea, the CD4 cell count and the CD4 cell category. This table demonstrates that the subjects in each group were similar.

TABLE 1

Baseline Characteristics in the Placebo-Controlled Treatment Phase

| Baseline Disease Characteristics | Placebo (N = 138) | Crofelmer 125 mg* (N = 138) | Crofelmer 250 mg (N = 54) | Crofelmer 500 mg (N = 47) | All Crofelmer (N = 239) |
|---|---|---|---|---|---|
| Cause of diarrhea | | | | | |
| Antiretroviral therapy | 104 (75.4%) | 104 (75.4%) | 37 (68.5%) | 30 (63.8%) | 171 (71.5%) |
| HIV infection of intestine | 33 (23.9%) | 32 (23.2%) | 15 (27.8%) | 15 (31.9%) | 62 (25.9%) |
| Other | 1 (0.7%) | 2 (1.4%) | 2 (3.7%) | 2 (4.3%) | 6 (2.5%) |
| CD4 cell counts | | | | | |
| n | 138 | 137 | 54 | 46 | 237 |
| Mean | 530.5 | 497.8 | 425.2 | 481.7 | 478.1 |
| SD | 244.79 | 230.88 | 226.13 | 275.18 | 239.81 |

TABLE 1-continued

Baseline Characteristics in the Placebo-Controlled Treatment Phase

| Baseline Disease Characteristics | Placebo (N = 138) | Crofelmer 125 mg* (N = 138) | Crofelmer 250 mg (N = 54) | Crofelmer 500 mg (N = 47) | All Crofelmer (N = 239) |
|---|---|---|---|---|---|
| Median | 518.5 | 479.0 | 374.0 | 421.5 | 429.0 |
| Min | 76 | 111 | 100 | 149 | 100 |
| Max | 1298 | 1183 | 1095 | 1734 | 1734 |
| CD4 cell Category | | | | | |
| <404 | 39 (28.3%) | 55 (39.9%) | 29 (53.7%) | 21 (44.7%) | 105 (3.9%) |
| >=404 | 99 (71.7%) | 32 (59.4%) | 25 (46.3%) | 25 (53.2%) | 132 (55.2%); |

[1] Baseline was the average of daily data from the 7 days prior to first dose day of randomized study drug.
[2] Baseline was the average of daily stool consistency scores from the 7 days prior to first dose day of randomized study drug. The daily score = (1*# of very hard stools + 2*# of hard stools + 3*# of formed stools + 4*# of loose stools + 5*# of watery stools)/(# of total stools).
[3] Baseline was the average of daily scores from the 7 days prior to first dose day of randomized study drug, none = 0, mild = 1, moderate = 2, severe = 3.
[4] Baseline = 7*A/B, A = # of days with event during the 7 days prior to first dose day of randomized study drug, B = # of days with non-missing assessments.

Table 2 below shows additional baseline characteristics of the placebo-controlled treatment phase, including use of antibiotics during the study.

TABLE 2

Baseline Characteristics of the Placebo-Controlled Treatment Phase

| Baseline Disease Characteristics | Placebo (N = 138) | Crofelmer 125 mg* (N = 138) | Crofelmer 250 mg (N = 54) | Crofelmer 500 mg (N = 47) | All Crofelmer (N = 239) |
|---|---|---|---|---|---|
| Use of a new antibiotic regimen during placebo-controlled treatment phase | | | | | |
| Yes | 14 (10.1%) | 9 (6.5%) | 2 (3.7%) | 1 (2.1%) | 12 (5.0%) |
| No | 124 (89.9%) | 129 (92.5%) | 52 (96.3%) | 46 (97.9%) | 227 (95.0%) |

Tables 3 and 3a below show the percentage of subjects with clinical response, e.g., improvement of watery diarrhea, in the placebo-controlled treatment phase, and the change in response from baseline as a function of time, respectively. As can be seen from Table 3, all three treatment groups from Stage I were statistically significant for treatment of watery diarrhea, as well at the combined group of subjects dosed 125 mg in both stages. Table 3a sets forth data indicating that, regardless of treatment group, the primary endpoint (Clinical Response) demonstrated responsiveness by consistently correlating with other daily assessments collected in the study for changes in symptoms scoring. Responders, i.e., subjects with ≤2 watery stools per week, had significantly greater improvements in daily symptom severity scores than non-responders at each week during the course of the study.

TABLE 3

Primary Efficacy Endpoint: Percentage of Subjects with Clinical Response in the Placebo-Controlled Treatment Phase

| | Placebo (N = 138) | Crofelmer 125 mg* (N = 136) | Crofelmer 250 mg (N = 54) | Crofelmer 500 mg (N = 46) |
|---|---|---|---|---|
| Stage I | | | | |
| Responder-n/Ni (%) | 1/50 (2.0%) | 9/44 (20.5%) | 5/54 (9.3%) | 9/46 (19.6%) |
| Treatment Difference (vs. Placebo) | | 18.5% | 7.3% | 17.6% |
| 1-Sided 97.5% CI (1) | | (6.0%, 00) | (−1.7%, 00) | (5.3%, 00) |
| 1-Sided P-value (vs. Placebo) [1] | | 0.0019 | 0.0563 | 0.0024 |
| Combined | | | | |
| Responder-n/Ni (%) | 11/138 (8.0%) | 24/136 (17.6%) | | |
| Treatment Difference (vs. Placebo) | | 9.6% | | |
| 1-Sided 97.5% CI (1) | | (1.2%, 00) | | |
| 1-Sided P-value (vs. Placebo) [1] | | 0.0096 | | |

TABLE 3a

Responsiveness of the Primary Endpoint (Clinical Response) -

| Week | Daily Question | Clinical Response[a]: Weekly Responder Mean Change from Baseline (±SD) | Clinical Response[a]: Weekly Non-Responder Mean Change from Baseline (±SD) | Difference Responder - Non-Responder | p-value |
|---|---|---|---|---|---|
| Week 1 | | | | | |
| | Daily Watery Stools | −1.75 (0.901) | −0.51 (1.296) | −1.24 | <0.0001 |
| | Daily Stool Consistency[b] | −1.08 (0.589) | −0.19 (0.381) | −0.90 | <0.0001 |
| | Daily Abdominal Pain[c] | −0.41 (0.651) | −0.11 (0.493) | −0.30 | 0.0217 |
| | Urgency[d] | −2.97 (2.299) | −0.75 (1.908) | −2.22 | <0.0001 |
| | Fecal Incontinence[e] | −1.48 (2.007) | −0.43 (1.867) | −1.06 | 0.0144 |
| | Daily Stool Frequency | −1.13 (1.299) | −0.31 (1.810) | −0.83 | <0.0001 |
| Week 2 | | | | | |
| | Daily Watery Stools | −2.03 (1.184) | −0.53 (1.392) | −1.50 | <0.0001 |
| | Daily Stool Consistency[b] | −1.14 (0.672) | −0.17 (0.379) | −0.97 | <0.0001 |
| | Daily Abdominal Pain[c] | −0.61 (0.701) | −0.12 (0.494) | −0.49 | <0.0001 |
| | Urgency[d] | −2.79 (2.418) | −0.79 (2.014) | −2.00 | <0.0001 |
| | Fecal Incontinence[e] | −1.71 (2.071) | −0.44 (1.982) | −1.27 | <0.0001 |
| | Daily Stool Frequency | −1.18 (1.331) | −0.34 (1.851) | −0.83 | <0.0001 |
| Week 3 | | | | | |
| | Daily Watery Stools | −2.00 (1.280) | −0.65 (1.408) | −1.35 | <0.0001 |
| | Daily Stool Consistency[b] | −1.20 (0.734) | −0.22 (0.382) | −0.98 | <0.0001 |
| | Daily Abdominal Pain[c] | −0.51 (0.668) | −0.17 (0.517) | −0.34 | 0.0016 |
| | Urgency[d] | −3.41 (2.215) | −0.98 (2.253) | −2.43 | <0.0001 |
| | Fecal Incontinence[e] | −1.65 (2.228) | −0.64 (2.121) | −1.01 | 0.0015 |
| | Daily Stool Frequency | −1.20 (1.314) | −0.41 (1.992) | −0.79 | <0.0001 |
| Week 4 | | | | | |
| | Daily Watery Stools | −1.89 (1.058) | −0.68 (1.430) | −1.21 | <0.0001 |
| | Daily Stool Consistency[b] | −1.07 (0.645) | −0.24 (0.410) | −0.83 | <0.0001 |
| | Daily Abdominal Pain[c] | −0.48 (0.658) | −0.19 (0.533) | −0.28 | 0.0058 |
| | Urgency[d] | −3.11 (2.411) | −0.99 (2.166) | −2.12 | <0.0001 |
| | Fecal Incontinence[e] | −1.75 (2.140) | −0.57 (2.085) | −1.18 | <0.0001 |
| | Daily Stool Frequency | −1.07 (1.086) | −0.43 (2.039) | −0.64 | <0.0001 |

[a] Clinical response in a week was defined as ≤2 watery stools during a given week.
[b] Stool consistency response was defined as <4 daily stool consistency score during a given week
[c] Abdominal pain and discomfort score: 0 = none, 1 = mild, 2 = moderate, and 3 = severe.
[d] Number of days per week with urgency = 7*A/B, where A = # of days with urgency in the week, and B = # of days with assessments in the week.
[e] Number of days per week with fecal incontinence = 7*A/B, where A = # of days with fecal incontinence in the week, and B = # of days with assessments in the week.
[f] P-values were obtained from a Wilcoxon rank-sum test for comparison of the responder vs. non-responder groups.

Table 4 below shows the number of weeks of clinical response of subjects in the study. As shown below, the subjects dosed with 500 mg BID had more weeks of response to the treatment.

TABLE 4

Number of Weeks with Clinical Response in the Placebo-Controlled Treatment Phase

| Number of Weeks Responded | Placebo (N = 138) | Crofelmer 125 mg* (N = 136) | Crofelmer 250 mg (N = 54) | Crofelmer 500 mg (N = 46) |
|---|---|---|---|---|
| Stage I | | | | |
| Number of Subjects | N = 50 | N = 44 | N = 54 | N = 46 |
| 0 week | 43 (86.0%) | 32 (72.7%) | 41 (75.9%) | 25 (60.9%) |
| 1 week | 6 (12.0%) | 2 (4.5%) | 8 (14.8%) | 9 (19.6%) |
| 2 weeks | | 2 (4.5%) | 2 (3.7%) | 4 (8.7%) |
| 3 weeks | | 4 (9.1%) | 2 (3.7%) | 4 (8.7%) |
| 4 weeks | 1 (2.0%) | 3 (6.8%) | 1 (1.9%) | 1 (2.2%) |
| Crofelmer vs. Placebo [1] | | | | |
| Odds Ratio | | 2.41 | 2.02 | 4.21 |
| 95% CI | | (0.84, 6.87) | (0.74, 5.56) | (1.56, 11.33) |
| p-value | | 0.1011 | 0.1727 | 0.0045 |

Table 5 below shows subjects with clinical response by month. As can be seen from the Table, responding subjects and response rate increases the longer a subject was administered crofelemer.

TABLE 5

Subjects with Monthly Clinical Response by Month in the Placebo-Free Extension Phase

| Responders in Placebo-free Extension Phase | Crofelmer 125 mg* (N = 219) n (%) | Crofelmer 250 mg (N = 68) n (%) | Crofelmer 500 mg (N = 50) n (%) | All Crofelmer (N = 337) n (%) |
|---|---|---|---|---|
| Month 1 | 87/218 (39.9%) | 19/68 (27.9%) | 14/50 (28.0%) | 120/336 (35.7%) |
| Month 2 | 99/208 (47.6%) | 31/60 (51.7%) | 19/48 (39.6%) | 149/316 (47.2%) |
| Month 3 | 111/198 (56.1%) | 30/58 (51.7%) | 17/47 (36.2%) | 158/303 (52.1%) |
| Month 4 | 99/178 (55.6%) | 27/54 (50.0%) | 20/44 (45.5%) | 146/276 (52.9%) |
| Month 5 | 90/155 (58.1%) | 30/53 (56.6%) | 17/42 (40.5%) | 137/250 (54.8%) |

Table 6 below shows the percent of subjects with stool consistency response to crofelemer. As can be seen from Table 6, subjects administered 500 mg and 250 mg BID responded better than did the 125 mg BID or the 250 mg BID.

TABLE 6

Percentage of Subjects with Stool Consistency Response in the Placebo-Controlled Treatment Phase

| | Placebo (N = 138) | Crofelmer 125 mg* (N = 136) | Crofelmer 250 mg (N = 54) | Crofelmer 500 mg (N = 46) |
|---|---|---|---|---|
| Stage I | | | | |
| Responder-n/Ni (%) | 11/50 (22.0%) | 14/44 (31.8%) | 20/54 (37.0%) | 23/46 (50.0%) |
| Treatment Difference vs. Placebo | | 9.8% | 15.0% | 28.0% |
| 1-Sided 97.5% CI [1] | | (−8.1%, $^{00}$) | (−2.6%, $^{00}$) | (−8.8%, $^{00}$) |
| 1-Sided P-value (vs. Placebo) [1] | | 0.1412 | 0.0470 | 0.0021 |
| Combined | | | | |
| Responder-n/Ni (%) | 49/186 (35.5%) | 53/136 (39.0%) | | |
| Treatment Difference vs. Placebo | | 3.5% | | |
| 1-Sided 97.5% CI [1] | | [−5.0%, $^{00}$) | | |
| 1-Sided P-value (vs. Placebo) [1] | | 0.1428 | | |

Table 7 below shows the number of months of clinical response by subjects on crofelemer in the study. Table 7 again demonstrates that the longer the treatment, the better the response to treatment.

TABLE 7

Number of Months with Clinical Response in the Placebo-Free Extension Phase

| Number of Weeks Responded | Crofelmer 125 mg* (N = 219) | Crofelmer 250 mg (N = 66) | Crofelmer 500 mg (N = 50) |
|---|---|---|---|
| 0 month | 69 (31.5%) | 25 (36.8%) | 25 (50.0%) |
| 1 month | 31 (14.2%) | 6 (8.8%) | 4 (8.0%) |
| 2 months | 19 (8.7%) | 10 (14.7%) | 4 (8.0%) |
| 3 months | 29 (13.2%) | 7 (10.3%) | 3 (6.0%) |
| 4 months | 25 (11.4%) | 10 (14.7%) | 4 (8.0%) |
| 5 months | 46 (21.0%) | 10 (14.7%) | 10 (20.0%) |

Table 8 below shows the percentage of Caucasian and Hispanic subjects and all other races with clinical response. This table demonstrates that the Caucasian and Hispanic populations receiving crofelemer responded well to treatment.

TABLE 8

Percentage of Subjects with Clinical Response by Race in the Placebo-Controlled Treatment Phase

| Race: White/Hispanic | Placebo (N = 83) | Crofelmer 125 mg* (N = 84) | Crofelmer 250 mg (N = 44) | Crofelmer 500 mg (N = 38) |
|---|---|---|---|---|
| Stage I | | | | |
| Responder - n/Ni (%) | 0/36 (0.0%) | 7/31 (22.6%) | 3/44 (6.8%) | 8/38 (21.1%) |
| Treatment Difference vs. Placebo | | 22.6% | 6.5% | 21.1% |
| [95% CI] | | [7.9%, 37.3%] | [−0.6%, 14.3%] | [8.14%, 34.0%] |
| P-value vs. Placebo [1] | | 0.0030 | 0.2481 | 0.0053 |
| Combined | | | | |
| Responder - n/Ni (%) | 6/83 (7.2%) | 19/84 (22.6%) | | |
| Treatment Difference vs. Placebo | | 15.4% | | |
| [95% CI] | | [4.9%, 25.9%] | | |
| P-value (vs. Placebo) [1] | | 0.0083 | | |

TABLE 8-continued

Percentage of Subjects with Clinical Response by Race in the
Placebo-Controlled Treatment Phase

| Race: White/Hispanic | Placebo (N = 83) | Crofelmer 125 mg* (N = 84) | Crofelmer 250 mg (N = 44) | Crofelmer 500 mg (N = 38) |
|---|---|---|---|---|
| Stage I | | | | |
| Responder - n/Ni (%) | 1/14 (7.1%) | 2/13 (15.4%) | 2/10 (20.0%) | 1/8 (12.5%) |
| Treatment Difference vs. Placebo | | 8.2% | 12.9% | 5.4% |
| [95% CI] | | [−15.6%, 32.0%] | [−15.4%, 41.1%] | [−21.2%, 32.0%] |
| P-value vs. Placebo [1] Combined | | 0.5956 | 0.5504 | 1.0000 |
| Responder - n/Ni (%) | 5/55 (9.1%) | 5/52 (9.6%) | | |
| Treatment Difference vs. Placebo | | 0.5% | | |
| [95% CI] | | [−10.5%, 11.6%] | | |
| P-value (vs. Placebo) [1] | | 1.0000 | | |

Note:
Clinical response was defined as <=2 watery stools per week during at least 2 of the 4 efficacy assessment weeks.
Note:
Percentage is based on Ni, number of subjects entered the stage or combine.

In another study, 400 subjects with chronic HIV associated diarrhea were treated with crofelmer or placebo for 7 days in an inpatient setting. Crofelmer was given at doses of 250 mg and 500 mg enteric-coated tablets or 500 mg enteric-coated beads four times daily, compared to a matching placebo. Subjects who responded to treatment were continued in a three-week blinded outpatient phase. The difference in decreased stool weight between subjects receiving crofelmer and subjects receiving placebo was not statistically significant by the primary efficacy analysis.

However, reanalysis of these data revealed that approximately 50% of the study population did not have watery diarrhea at study entry. Evaluation of the population with watery diarrhea and urgency at baseline revealed statistically significant improvement in stool frequency and weight (p<0.05) with treatment. Changes in abnormal (watery and loose) stools were even greater, with significant (p<0.015) improvements in abnormal stool weight and frequency observed at Day 7. Approximately 3 days were necessary for the anti-diarrheal effects of crofelmer to stabilize.

Table 9 below shows additional supportive data showing that crofelmer 125 mg, 250 mg and 500 mg were efficacious at treating HIV associated diarrhea.

TABLE 9

Primary Efficacy Endpoint
Percentage of Subjects with Clinical Response*

| | Placebo (N = 138) | Crofelmer 125 mg (N = 136) | Crofelmer 250 mg (N = 54) | Crofelmer 500 mg (N = 46) |
|---|---|---|---|---|
| Stage 1 | | | | |
| Responder | 1/50 (2.0%) | 9/44 (20.5%) | 5/54 (9.3%) | 9/46 (19.6%) |
| Treatment Difference | | 18.50% | 7.30% | 17.60% |

TABLE 9-continued

Primary Efficacy Endpoint
Percentage of Subjects with Clinical Response*

| | Placebo (N = 138) | Crofelmer 125 mg (N = 136) | Crofelmer 250 mg (N = 54) | Crofelmer 500 mg (N = 46) |
|---|---|---|---|---|
| Stage 2 | | | | |
| Responder | 10/88 (11.4%) | 15/92 (16.3%) | | |
| Treatment Difference Combined | | 4.90% | | |
| Responder | 11/138 (8.0%) | 24/136 (17.6%) | | |
| Treatment Difference | | 9.60% | | |
| 1-Sided 97.5% CI | | [1.2%, ∞) | | |
| 1-Sided P-value (vs. Placebo) | | 0.0096 | | |

*≤2 watery BM/wk during ≥2 of 4 wks of the 4-wk placebo controlled period

Table 10 below shows that crofelmer is particularly efficacious in treating males with HIV associated diarrhea. Additional subgroup analysis is shown in FIG. 1. The primary endpoint was analyzed in subgroups defined by demographics and baseline characteristics to assess the consistency of the treatment effect. FIG. 1 provides a summary of each of these subgroup analyses, showing the treatment difference in percentage of responders (crofelmer 125 mg BID vs. placebo) with associated confidence intervals and p-values. As shown in the figure, consistent efficacy was observed across subgroups; a higher percentage of subjects treated with crofelmer 125 mg BID experienced clinical response compared with placebo in all subgroups analyzed.

TABLE 10

Effects Across Demographic & Baseline Characteristics-Gender*

| | Placebo (N = 138) | Crofelmer 125 mg (N = 136) |
|---|---|---|
| Gender: Male | | |
| Responder - n/Ni (%) | 9/116 (7.8%) | 22/115 (19.1%) |
| Treatment Difference vs Placebo | | 11.40% |
| [95% CI] | | [2.7%, 20.1%] |
| P-value vs Placebo | | 0.0124 |
| Gender: Female | | |
| Responder - n/Ni (%) | 2/22 (9.1%) | 2/21 (9.5%) |
| Treatment Difference vs Placebo | | 0.40% |
| [95% CI] | | [−16.9%, 17.8%] |
| P-value vs Placebo | | 1 |

*Clinical response was defined as <=2 watery stools per week during at least 2 of the 4 efficacy assessment weeks. Intent-to-Treat Population.

According to one aspect, provided herein are methods of treating HIV associated diarrhea or highly active antiretroviral therapy (HAART) associated diarrhea in a male HIV positive subject, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelmer to a male subject in need thereof.

Below, Table 11 shows that subject taking protease inhibitors responded particularly well to treatment with crofelmer.

TABLE 11

Effects Across Demographic & Baseline Characteristics-
Prior use of Protease Inhibitors*

|  | Placebo (N = 138) | Crofelemer 125 mg (N = 136) |
|---|---|---|
| Use of PI at Screening - Yes: | | |
| Responder - n/Ni (%) | 6/97 (6.2%) | 15/86 (17.4%) |
| Treatment Difference vs Placebo | | 11.30% |
| [95% CI] | | [1.9%, 20.6%] |
| P-value vs Placebo | | 0.0204 |
| Use of PI at Screening - No: | | |
| Responder - n/Ni (%) | 5/41 (12.2%) | 9/50 (18.0%) |
| Treatment Difference vs Placebo | | 5.80% |
| [95% CI] | | [−8.8%, 20.4%] |
| P-value vs Placebo | | 0.5638 |

*Clinical response was defined as <=2 watery stools per week during at least 2 of the 4 efficacy assessment weeks. Intent-to-Treat Population According to one aspect, provided herein are methods of treating HIV associated diarrhea or highly active antiretroviral therapy (HAART) associated diarrhea in an HIV positive subject that has previously used protease inhibitors, comprising: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer to a male subject in need thereof. As used herein, "previously used" includes, for example, subjects who have used protease inhibitors (PIs) prior to crofelemer therapy or overlapping with crofelemer therapy, but the PI use began prior to the first dose of crofelemer therapy.

TABLE 12

Secondary Efficacy Endpoints

| Intent-to-Treat Population | |
|---|---|
| Watery BMs/day | No treatment differences between 125 mg vs. Pbo Stage 1: numerically greater in 500 mg vs. Pbo (−0.91/day vs. −0.62/day; p = 0.0713) |
| Stool consistency score | Significant improvement for 125 mg vs. Pbo (−0.35 vs. −0.25; p = 0.0168) |
| Daily abd pain/discomfort | No treatment differences between 125 mg vs. Pbo Stage 1: 125 mg vs. Pbo (−0.35 vs. −0.13; p = 0.0170) |
| Days/wk with urgency | No treatment differences between 125 vs. Pbo |
| Days/wk with fecal incontinence | Numerical differences for 125 mg vs. Pbo (−0.96 vs. −0.55; p = 0.0643) |
| BMs/day | No treatment differences between 125 mg vs. Pbo |

FIG. 1 and Table 13 show subjects with clinical response in the crossover to placebo-free phase of the safety population. PC=Placebo-controlled Phase and PF=Placebo-free Phase. This data shows that subjects previously on placebo had a sharp increase in efficacy when they were crossed-over onto 125 mg crofelemer. This data also demonstrates that crofelemer efficacy continued to rise with length of use.

TABLE 13

Subjects with Clinical Response Crossover to
Placebo-Free Phase, Safety Population

| Month | Statistic[1] | Placebo (N = 126) | Crofelemer 125 mg (N = 99) | Crofelemer 250 mg (N = 15) | Crofelemer 500 mg (N = 12) |
|---|---|---|---|---|---|
| Month 1 | Responder - n/Ni (%) | 11/126 (8.7%) | 36/99 (36.4%) | 3/15 (20.0%) | 2/12 (16.7%) |
| | Odds Ratio (95% CI) | | 0.17 (0.09, 0.32) | | |
| | P-value (vs. Placebo in PC) | | <.0001 | | |
| Month 2 | Responder - n/Ni (%) | | 42/95 (44.2%) | 8/15 (53.3%) | 2/12 (16.7%) |
| | Odds Ratio (95% CI) | | 0.12 (0.06, 0.24) | | |
| | P-value (vs. Placebo in PC) | | <.0001 | | |
| Month 3 | Responder - n/Ni (%) | | 48/89 (53.9%) | 5/14 (35.7%) | 2/11 (18.2%) |
| | Odds Ratio (95% CI) | | 0.07 (0.03, 0.15) | | |
| | P-value (vs. Placebo in PC) | | <.0001 | | |
| Month 4 | Responder - n/Ni (%) | | 43/77 (55.8%) | 5/13 (38.5%) | 2/9 (22.2%) |
| | Odds Ratio (95% CI) | | 0.07 (0.03, 0.15) | | |
| | P-value (vs. Placebo in PC) | | <.0001 | | |
| Month 5 | Responder - n/Ni (%) | | 37/67 (55.2%) | 6/13 (46.2%) | 1/8 (12.5%) |
| | Odds Ratio (95% CI) | | 0.07 (0.03, 0.16) | | |
| | P-value (vs. Placebo in PC) | | <.0001 | | |

[1] Ratio of responders and p value obtained from parameter estimates with effect for treatment and region.

TABLE 14

Subjects with Stool Consistency Response*
Intent-to-Treat Population

| | Placebo (N = 138) | Crofelemer 125 mg (N = 136) | Crofelemer 250 mg (N = 54) | Crofelemer 500 mg (N = 46) |
|---|---|---|---|---|
| Stage 1 | | | | |
| Responder | 11/50 (22.0%) | 13/44 (31.8%) | 20/54 (37.0%) | 23/46 (50.0%) |
| Treatment Difference | | 9.80% | 15.00% | 28.00% |
| Stage 2 | | | | |
| Responder | 38/88 (43.2%) | 39/92 (42.4%) | | |
| Treatment Difference | | −0.80% | | |
| Combined | | | | |
| Responder | 49/138 (35.5%) | 53/136 (39.0%) | | |
| Treatment Difference | | 3.50% | | |

*<4 stool consistency score at least 2 of the 4 efficacy assessment weeks.

Figure 2:
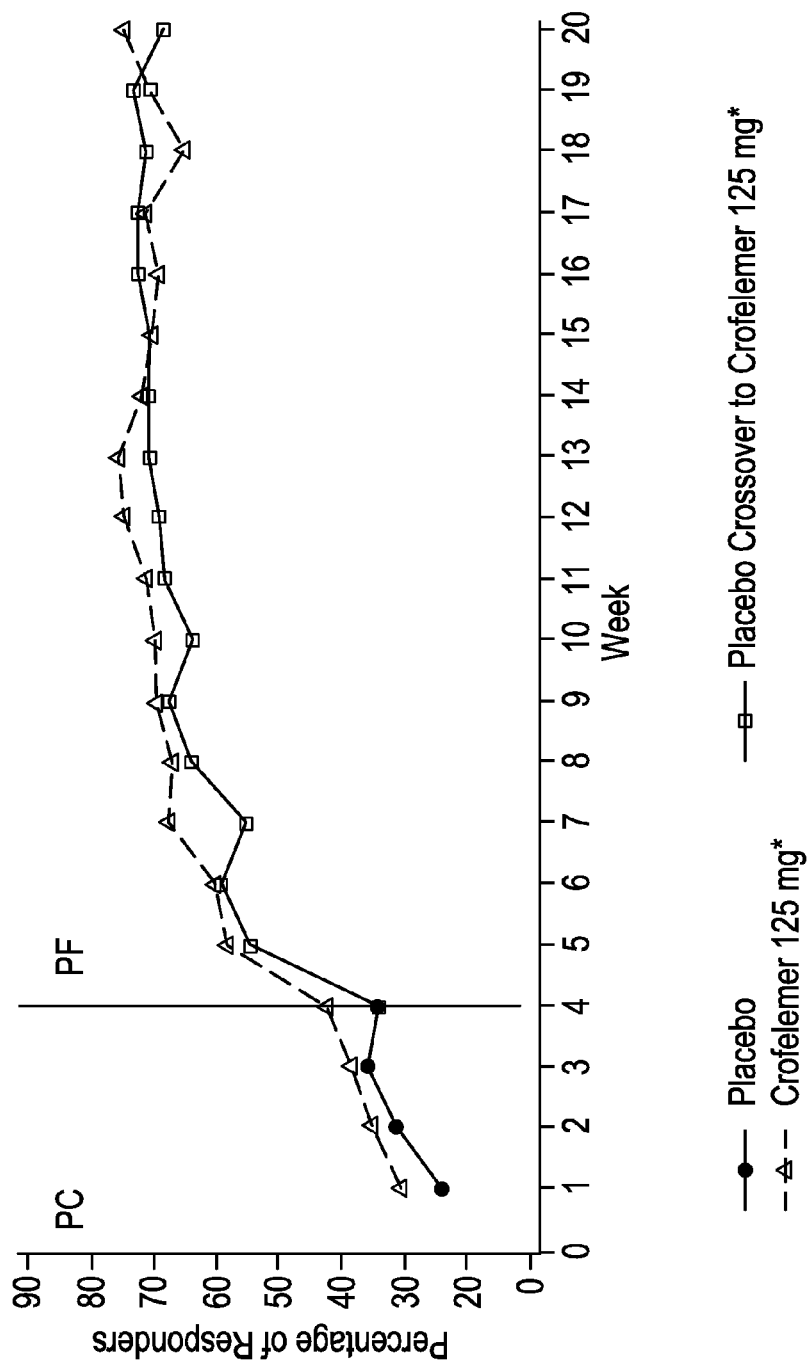
FIG. 2 shows subjects with stool consistency response in the crossover to placebo-free phase in the safety population.

FIG. 2 and Table 14 show subjects with stool consistency response in the crossover to placebo-free phase in the safety population. PC=Placebo-controlled Phase and PF=Placebo-free Phase. This data shows that subjects previously on placebo had a sharp increase in efficacy when they were crossed-over onto 125 mg crofelemer. This data also demonstrates that crofelemer efficacy continued to rise with length of use.

TABLE 15

Subjects With Abnormal ECG Findings
Safety Population

| Characteristic, n (%) | Placebo (N = 137) | Crofelemer 125 mg (N = 130) | Crofelemer 250 mg (N = 54) | Crofelemer 500 mg (N = 42) | All Crofelemer (N = 226) |
|---|---|---|---|---|---|
| Post Baseline Abnormal ECG Finding [1] | 35 (25.5%) | 34 (26.2%) | 18 (33.3%) | 13 (31.0%) | 65 (28.8%) |
| QT Interval (msec) | | | | | |
| >450 with Baseline ≤ 450 | 2 (1.5%) | 4 (3.1%) | 1 (1.9%) | 0 | 5 (2.2%) |
| >480 with Baseline ≤ 480 | 1 (0.7%) | 0 | 1 (1.9%) | 0 | 1 (0.4%) |
| >500 with Baseline ≤ 500 | 0 | 0 | 1 (1.9%) | 0 | 1 (0.4%) |
| Change from Baseline 30-60 | 9 (6.6%) | 4 (3.1%) | 6 (11.1%) | 3 (7.1%) | 13 (5.8%) |
| Change from Baseline > 60 | 4 (2.9%) | 1 (0.8%) | 2 (3.7%) | 0 | 3 (1.3%) |
| QT Interval Linear Regression Correction (msec) | | | | | |
| >450 with Baseline ≤ 450 | 2 (1.5%) | 4 (3.1%) | 1 (1.9%) | 0 | 5 (2.2%) |
| >480 with Baseline ≤ 480 | 1 (0.7%) | 0 | 1 (1.9%) | 0 | 1 (0.4%) |
| >500 with Baseline ≤ 500 | 0 | 0 | 1 (1.9%) | 0 | 1 (0.4%) |
| Change from Baseline 30-60 | 7 (5.1%) | 4 (3.1%) | 6 (11.1%) | 3 (7.1%) | 13 (5.8%) |
| Change from Baseline > 60 | 4 (2.9%) | 1 (0.8%) | 2 (3.7%) | 0 | 3 (1.3%) |
| QT Interval Fridericias's Correction (msec) | | | | | |
| >450 with Baseline ≤ 450 | 6 (4.4%) | 1 (0.8%) | 2 (3.7%) | 0 | 3 (1.3%) |
| >480 with Baseline ≤ 480 | 1 (0.7%) | 1 (0.8%) | 0 | 0 | 1 (0.4%) |
| >500 with Baseline ≤ 500 | 1 (0.7%) | 0 | 0 | 0 | 0 |
| Change from Baseline 30-60 | 3 (2.2%) | 5 (3.8%) | 2 (3.7%) | 1 (2.4%) | 8 (3.5%) |
| Change from Baseline > 60 | 4 (2.9%) | 0 | 1 (1.9%) | 0 | 1 (0.4%) |
| QT Interval Bazett's Correction (msec) | | | | | |
| >450 with Baseline ≤ 450 | 8 (5.8%) | 4 (3.1%) | 2 (3.7%) | 0 | 6 (2.7%) |
| >480 with Baseline ≤ 480 | 2 (1.5%) | 2 (1.5%) | 1 (1.9%) | 0 | 3 (1.3%) |
| >500 with Baseline ≤ 500 | 2 (1.5%) | 0 | 0 | 0 | 0 |
| Change from Baseline 30-60 | 7 (5.1%) | 8 (6.2%) | 3 (5.6%) | 1 (2.4%) | 12 (5.3%) |
| Change from Baseline > 60 | 3 (2.2%) | 1 (0.8%) | 1 (1.9%) | 0 | 2 (0.9%) |

Table 15 demonstrates that crofelemer is safe to be given to subjects and that there are no QT Interval issues associated with use. This is surprising and advantageous over other molecules used to treat diarrhea and IBS, which are know to be associated with QT issues.

From the above data and Figures, it has been demonstrated that the proportion of clinical responders was significantly higher in the crofelemer 125 mg group compared with placebo (p=0.0096; Combined data). Subjects switching from placebo to crofelemer upon conclusion of the placebo-controlled phase achieved rates of clinical response of between 36.4% and 55.8% for each of the 5 months of the placebo-free phase (p<0.0001; for data collected prior to lock). Stool consistency scores improved significantly in subjects receiving 125 mg crofelemer compared with placebo (p=0.0168; Combined data). Days per week that subjects experienced fecal incontinence decreased in subjects receiving 125 mg crofelemer compared with placebo (p=0.0643; Combined data). It is also demonstrated that crofelemer was well tolerated and demonstrated a safety profile comparable to placebo and no clinically important differences in safety assessments have been identified.

TABLE 16

Dose-Ranging Study for treatment of d-IBS:
All Randomized Subjects

| | |
|---|---|
| Design: | P2, R, DB, PC, Dose-Ranging Study for treatment of d-IBS |
| Treatment: | 125, 250, 500 mg Crofelemer b.i.d. or Pbo for 12 weeks |
| N: | 125 mg: 62, 250 mg: 60, 250 mg: 62, Pbo: 61 |
| Primary Endpoint | Daily stool consistency |
| Outcome: | ROME Foundation Definition[1]  Month 1 = 2.6% |
| | Treatment Δ, 125 mg dose  Month 2 = 9.0% |
| | Month 3 = 10.7% |
| | All 3 months: Odds Ratio  1.51 (0.78, 2.92) |
| | FDA Definition[2]  Month 1 = 0.6% |
| | Treatment Δ, 125 mg dose  Month 2 = 2.2% |
| | Month 3 = −4.4% |
| | All 3 months: Odds Ratio  1.09 (0.54, 2.20) |

[1]ROME Foundation Stool consistency weekly responder: Subjects with <25% days with loose or watery stools in a given week. Based on Ad Hoc Table 1.1
[2]FDA Stool consistency weekly responder: Subjects with a weekly average stool consistency score <4 (4 = Loose stool)

Table 16 demonstrates that crofelemer is an efficacious treatment for d-IBS. It also demonstrates that crofelemer is an efficacious treatment for treating abnormal stool consistency associated with d-IBS.

In one embodiment, crofelemer is administered to treat abnormal stool consistency associated with d-IBS for at least one month.

In one embodiment, crofelemer is administered to treat abnormal stool consistency associated with d-IBS from between one month and two months or longer. In one embodiment, crofelemer is administered to treat abnormal stool consistency associated with d-IBS from between about one month and about three months or longer.

In one embodiment, crofelemer is administered to treat abnormal stool consistency associated with d-IBS for at least one month at about 125 mg b.i.d. In one embodiment, crofelemer is administered to treat abnormal stool consistency associated with d-IBS from between one month and two months or longer at about 125 mg b.i.d. In one embodiment, crofelemer is administered to treat abnormal stool consistency associated with d-IBS from between one month and three months or longer at about 125 mg b.i.d.

TABLE 17

Dose-Ranging Study for treatment of d-IBS
All Randomized Female Subjects

| | | |
|---|---|---|
| Design: | P2, R, DB, PC, Dose-Ranging Study for treatment of d-IBS | |
| Treatment: | 125, 250, 500 mg Crofelemer b.i.d. or Pbo for 12 weeks | |
| N (125 mg females): | 125 mg: 46, Pbo: 46 | |
| Primary Endpoint | Daily stool consistency | |
| Outcome: | ROME Foundation Definition[1] | Month 1 = 6.5% |
| | Treatment Δ, 125 mg dose | Month 2 = 10.8% |
| | | Month 3 = 10.8% |
| | All 3 months: Odds Ratio | 1.88 (0.87, 4.06) |
| | FDA Definition[2] | Month 1 = −2.1% |
| | Treatment Δ, 125 mg dose | Month 2 = 2.2% |
| | | Month 3 = −4.4% |
| | All 3 months: Odds Ratio | 1.20 (0.52, 2.75) |

[1]ROME Foundation Stool consistency weekly responder: Subjects with <25% days with loose or watery stools in a given week. Based on Ad Hoc Table 1.1
[2]FDA Stool consistency weekly responder: Subjects with a weekly average stool consistency score <4 (4 = Loose stool)

Table 17 demonstrates that crofelemer is an efficacious treatment for d-IBS, especially to treat d-IBS in females. It also demonstrates that crofelemer is an efficacious treatment for treating abnormal stool consistency associated with d-IBS, and especially to treat abnormal stool consistency associated with d-IBS in females.

In one embodiment, crofelemer is administered to treat abnormal stool consistency associated with d-IBS in females for at least one month at 125 mg b.i.d. In one embodiment, crofelemer is administered to treat abnormal stool consistency associated with d-IBS in females from between one month and two months at about 125 mg b.i.d. In one embodiment, crofelemer is administered to treat abnormal stool consistency associated with d-IBS in females from between one month and three months or longer at about 125 mg b.i.d.

Table 18 demonstrates that crofelemer is an efficacious treatment for d-IBS, especially to treat d-IBS in females. It also demonstrates that crofelemer is an efficacious treatment for treating abdominal pain associated with d-IBS, and especially to treat abdominal pain associated with d-IBS in females.

In one embodiment, crofelemer is administered to treat d-IBS for at least one month.

In one embodiment, crofelemer is administered to treat d-IBS from between one month and two months or longer. In one embodiment, crofelemer is administered to treat d-IBS from between about one month and about three months or longer.

In one embodiment, crofelemer is administered to treat d-IBS for at least one month at about 125 mg b.i.d. In one embodiment, crofelemer is administered to treat d-IBS from between one month and two months or longer at about 125 mg b.i.d. In one embodiment, crofelemer is administered to treat d-IBS from between one month and three months or longer at about 125 mg b.i.d.

In one embodiment, crofelemer is administered to treat d-IBS in females for at least one month at 125 mg b.i.d. In one embodiment, crofelemer is administered to treat d-IBS in females from between one month and two months at about 125 mg b.i.d. In one embodiment, crofelemer is administered to treat d-IBS in females from between one month and three months or longer at about 125 mg b.i.d.

In one embodiment, crofelemer is administered to treat abdominal pain associated with d-IBS for at least one month.

In one embodiment, crofelemer is administered to treat abdominal pain associated with d-IBS from between one month and two months or longer. In one embodiment, crofelemer is administered to treat abdominal pain associated with d-IBS from between about one month and about three months or longer.

In one embodiment, crofelemer is administered to treat abdominal pain associated with d-IBS for at least one month at about 125 mg b.i.d. In one embodiment, crofelemer is administered to treat abdominal pain associated with d-IBS from between one month and two months or longer at about 125 mg b.i.d. In one embodiment, crofelemer is administered to treat abdominal pain associated with d-IBS from between one month and three months or longer at about 125 mg b.i.d.

In one embodiment, crofelemer is administered to treat abdominal pain associated with d-IBS in females for at least one month at 125 mg b.i.d. In one embodiment, crofelemer is administered to treat abdominal pain associated with d-IBS in females from between one month and two months at about 125 mg b.i.d. In one embodiment, crofelemer is administered

TABLE 18

Dose-Ranging Study for treatment of d-IBS in females
All Randomized Subjects

| | | | |
|---|---|---|---|
| Design: | P2, R, DB, PC, Dose-Ranging Study for treatment of d-IBS in females | | |
| Treatment: | 125 mg Crofelemer b.i.d. or Pbo for 12 weeks | | |
| N: | 125 mg: 120, Pbo: 120 | | |
| Primary Endpoint | Daily abdominal pain[1] | | |
| Outcome: | Placebo (N = 120) | 125 mg (N = 120) | P-value |
| Month 1 | 66 (55.0%) | 75 (62.5%) | 0.2316 |
| Month 2 | 61 (50.8%) | 82 (68.3%) | 0.0059 |
| Month 3 | 65 (54.2%) | 79 (65.8%) | 0.0662 |
| All 3 Months | Odds Ratio: 1.67 (1.03, 2.70); p = 0.0357 | | |

[1]Abdominal pain weekly responder is defined as subjects with at least 30% improvement compared to baseline abdominal pain score in a given week to treat abdominal pain associated with d-IBS in females from between one month and three months or longer at about 125 mg b.i.d.

Example 10

A Double-Blind, Randomized, Placebo-Controlled, Phase II Study to Assess the Safety and Efficacy of Orally Administered Crofelemer for the Symptomatic Treatment of Diarrhea in Acquired Immunodeficiency Syndrome (AIDS) Patients This study was a randomized, double-blind, multicenter (2 study sites), placebo-controlled, parallel-group study designed to assess the efficacy and safety of crofelemer 500 mg beads in subjects with HIV-associated diarrhea.

The primary objectives of the study were to evaluate the safety and efficacy of orally administered crofelemer for 96 hours for the symptomatic treatment of diarrhea in AIDS patients. The secondary objectives were 1) to characterize stool chloride ion concentration and daily stool chloride output in AIDS patients with diarrhea, 2) to compare stool chloride ion concentration and daily stool chloride output in AIDS patients with diarrhea treated with crofelemer or placebo, and 3) to assess stool consistency in AIDS patients with diarrhea treated with crofelemer or placebo.

There were 3 assessment periods during the study: 1) a 24-hour in-patient screening period to ensure that the subjects met all of the study criteria, during which baseline stool weight was assessed; 2) a 4-day inpatient treatment period, during which all subjects received their assigned treatment 4 times per day (Days 1-4); subjects were discharged from the hospital after 96 hours of treatment if clinically stable); and 3) a follow-up visit 7-9 days after discharge from the hospital. The use of ADM was not allowed during the study.

Efficacy measurements included assessments of stool weight and frequency, abnormal stool frequency, DGIS, MORE, body weight, time to diarrhea recurrence, and number of early dropouts (prior to completion of 4 days of treatment).

Efficacy endpoints in this study were as follows:

The primary efficacy endpoint in this study was the change in total daily stool weight during the Treatment Period. The secondary efficacy endpoints of the study were abnormal stool frequency, defined as watery or soft stools (change in daily abnormal stool frequency), stool frequency (change in daily stool frequency), DGIS (change from baseline in DGIS for each day [Days 1 through 4]), stool chloride concentration (mg chloride/g stool weight; change in daily stool chloride concentration) and measure of relief scores, where MORE was the maximum of: a) time from the start of treatment period to the first abnormal stool, b) the maximum time between abnormal stools, or c) the time between the last abnormal stool and the end of the treatment period.

The DGIS was the daily sum of mean symptom scores for each of 7 symptoms (nausea, vomiting, abdominal pain and/or cramps, excess gas, urgency, tenesmus, and incontinence) scored 4 times per day. Symptoms were rated on a 4-point scale from 0=absent to 3=severe.

A total of 85 subjects were enrolled into the study at 2 study sites. Two of subjects in each of the 2 treatment groups withdrew before completion of the in-patient treatment period.

All randomized subjects (n=85) received at least 1 dose of study drug and were included in efficacy analyses.

TABLE 19

Demographics:

| Characteristic Category or Statistic | Placebo (n = 42) | Crofelemer 500 mg Beads (n = 43) |
|---|---|---|
| Age, Years | | |
| Mean (±SD) | 38.9 (7.6) | 41.0 (8.8) |
| Median | 36 | 40 |
| Min, Max | 27, 55 | 21, 60 |
| Sex, n (%) | | |
| Male | 41 (97.6)) | 42 (97.7) |
| Female | 1 (2.4) | 1 (2.3) |
| Race, n (%) | | |
| Caucasian | 26 (61.9) | 32 (74.4) |
| Hispanic | 7 (16.7) | 6 (14.0) |
| African American | 7 (16.7) | 5 (11.6) |
| Other | 2 (5.0) | 0 |

Abbreviations:
ITT = intent-to-treat;
Max = maximum;
Min = minimum,
SD = standard deviation.

The number of unformed (i.e., soft or watery) stools/day at baseline (screening [Day 0]) and during the week prior to baseline, and disease severity are presented in Table. Mean (±SD) unformed stools/day at baseline was 5.5 (3.3) in the placebo group and 4.6 (2.6) in the crofelemer group. Most subjects had mild (3-4 stools/day) or moderate (5-8 stools/day) disease severity at baseline. Five subjects in the crofelemer group and 4 subjects in the placebo group had severe diarrhea (>9 stools/day).

TABLE 20

Baseline Diarrhea Assessments: (ITT Population)

| Characteristic Category or Statistic | Placebo (n = 42) | Crofelemer 500 mg Beads (n = 43) |
|---|---|---|
| Unformed Stools During 24 Hours Prior to First Dose of Study Drug (Screening [Day 0]), Stools/Day | | |
| Mean (±SD) | 5.6 (2.9) | 4.6 (2.5) |
| Median | 5 | 4 |
| Min, Max | 1, 6 | 0, 10 |
| Unformed Stools During the Week Prior to First Dose of Study Drug (Screening [Day 0]), Stools/Day | | |
| Mean (±SD) | 5.5 (2.9) | 5.1 (2.3) |
| Median | 6 | 5 |
| Min, Max | 1, 15 | 2, 10 |
| Diarrhea Severity, n (%) | | |
| Mild (3-4 stools/day) | 10 (40.0) | 15 (57.1) |
| Moderate (5-8 stools/day) | 13 (52.0) | 8 (30.8) |
| Severe (>9 stools/day) | 2 (8.0) | 3 (11.5) |

Abbreviations:
ITT = intent-to-treat;
Max = maximum;
Min = minimum,
SD = standard deviation.

Concomitant antiretroviral medications were received by majority of subjects (71 of 85): 36 of 42 (85.7%) in the placebo group and 35 of 43 (81.4%) in the crofelemer group. Protease inhibitors were taken by 69.4% of subjects. The concomitant use of antiretrovirals, including protease inhibitors, was balanced between groups.

The primary efficacy analysis was change in total daily stool weight during the 4-day in-patient treatment period. The primary endpoint of reduction in stool weight is an appropriate measure of the extent of watery diarrhea in patients with HIV-associated diarrhea due to high water content in the diarrhea experienced by these patients.

As shown in Table 21, there were significantly greater decreases in stool weight from baseline to Day 4 (last treatment day) in the crofelemer group compared with placebo (p=0.0335 by generalized linear model) in the ITT population. The repeated measures analysis of longitudinal data over the course of the 4-day Treatment Period did not show significant improvements in the crofelemer group compared to placebo; p=0.4108 for changes in total stool weight.

TABLE 21

Change in Stool Weight

| In-Patient Period | Placebo (n = 42) | Crofelemer 500 mg Beads (n = 43) | p-value (vs. Placebo)[a] |
|---|---|---|---|
| Stool Weight at Baseline (g) | | | |
| Mean (±SD) | 730.9 (720.14) | 861.3 (604.67) | 0.3832 |
| Median | 547.0 | 707.7 | |
| Min, Max | 206, 4701 | 220, 3407 | |
| Categories of Stool Weight at Baseline, n (%) | | | |
| Low (<740 g) | 28 (66.7) | 24 (55.8) | 0.2725 |
| High (>740 g) | 14 (33.3) | 19 (44.2) | |
| Change in Stool Weight: Baseline to Day 4 (g) | | | |
| Mean (±SD) | −192.4 (381.57) | −401.3 (531.65) | 0.0335 |
| Median | −232.8 | −267.5 | |
| Min, Max | −1319, 683 | −1815, 854 | |

Abbreviations:
ITT = intent-to-treat;
Max = maximum;
Min = minimum,
SD = standard deviation.
[a]P-value for baseline mean comparison is from generalized linear model with analysis center as a covariate. P-value for baseline percentage comparison is from CMH test with analysis center as a covariate. The estimates and p values are from the generalized linear model for the change from baseline result, with independent variables: treatment, analysis center, baseline category (value = Low for ≤740 g and High for >740 g in stool weight), and the interaction between treatment and baseline category (if p value > 0.15, the interaction term was not included).

The effect of crofelemer in decreasing stool weight was more pronounced in the subgroup of subjects with baseline stool weight >740 g when compared to subjects with baseline stool weight ≤740 g (p-values for differences relative to placebo were 0.0202 [>740 g subgroup] versus 0.6820 [≤740 g subgroup]).

There were significantly greater decreases from baseline in stool weight at Day 3 in the crofelemer group compared with placebo (p=0.0128).

Secondary Efficacy Results

Significantly greater decreases in the frequency of abnormal stools (i.e., watery or soft stools) from baseline to Day 4 were observed in the crofelemer group compared with placebo (p=0.0069 by generalized-linear model) in the ITT population. The repeated measures analysis of longitudinal data over the course of the Treatment Period also indicates significantly greater reductions in the crofelemer group compared with placebo; p=0.0330 for changes in abnormal stool frequency. In addition, subjects in the crofelemer group had significantly greater decreases in abnormal stool frequency from baseline to Day 2 (p=0.0454) and from baseline to Day 3 (p=0.0064) compared with subjects in the placebo group.

TABLE 22

Abnormal Stool Frequency

| In-Patient Period | Placebo (n = 42) | Crofelemer 500 mg Beads (n = 43) | p-value (vs. Placebo)[a] |
|---|---|---|---|
| Abnormal Stool (soft or watery stool) Frequency at Baseline; abnormal stools/day | | | |
| Mean (±SD) | 4.8 (2.12) | 4.9 (2.58) | 0.9933 |
| Median | 4.0 | 4.0 | |
| Min, Max | 3, 12 | 2, 14 | |
| Categories of Abnormal Stool Frequency at Baseline, n (%) | | | |
| Low (≤5/day) | 30 (71.4) | 32 (74.4) | 0.7847 |
| High (>5/day) | 12 (28.6) | 11 (25.6) | |
| Change in Abnormal Stool Frequency: Baseline to Day 4; abnormal stools/day | | | |
| Mean (±SD) | −2.1 (1.94) | −2.8 (2.23) | 0.0069 |
| Median | −2.0 | −3.0 | |
| Min, Max | −6, 4 | −11, 2 | |

Abbreviations:
ITT = intent-to-treat;
Max = maximum;
Min = minimum,
SD = standard deviation.
[a]P-value for baseline mean comparison is from generalized linear model with analysis center as a covariate. P-value for baseline percentage comparison is from CMH test with analysis center as a covariate. The estimates and p values are from the generalized linear model for the change from baseline result, with independent variables: treatment, analysis center, baseline category (value = Low for ≤5/day and High for >5/day in abnormal stool frequency), and the interaction between treatment and baseline category (if p value > 0.15, the interaction term was not included).

The effect of crofelemer in decreasing abnormal stool frequency was more pronounced in the subgroup with high abnormal stool counts at baseline (>5/day) compared to the subgroup with low abnormal stool counts at baseline (≤5/day; p-values for differences relative to placebo were 0.0041 [>5/day subgroup] versus 0.8184 [≤5/day subgroup])

Significantly greater decreases in stool frequency (i.e., formed, watery, and soft stools) from baseline to Day 4 were observed in the crofelemer group compared with placebo (p=0.0046 by generalized-linear model) in the ITT population (Table 23). The repeated measures analysis of longitudinal data over the course of the Treatment Period also indicates significantly greater reductions in the crofelemer group compared with placebo; p=0.0236 for changes in stool frequency.

The effect of crofelemer in decreasing stool frequency was more pronounced in the subgroup with high stool counts at baseline (>5/day) compared to the subgroup with low stool counts at baseline (≤5/day) (p-values for differences relative to placebo were 0.0019 [>5/day subgroup] versus 0.7912 [≤5/day subgroup]).

TABLE 23

Stool Frequency

| In-Patient Period | Placebo (n = 42) | Crofelemer 500 mg Beads (n = 43) | p-value (vs. Placebo)[a] |
|---|---|---|---|
| Stool Frequency at Baseline; stools/day | | | |
| Mean (±SD) | 5.1 (2.22) | 5.0 (2.46) | 0.8442 |
| Median | 4.0 | 4.0 | |
| Min, Max | 3, 12 | 2, 14 | |
| Categories of Stool Frequency at Baseline, n (%) | | | |
| Low (≤5/day) | 27 (64.3) | 32 (74.4) | 0.2850 |
| High (>5/day) | 15 (35.7) | 11 (25.6) | |

TABLE 23-continued

Stool Frequency

| In-Patient Period | Placebo (n = 42) | Crofelemer 500 mg Beads (n = 43) | p-value (vs. Placebo)$^a$ |
|---|---|---|---|
| Change in Stool Frequency: Baseline to Day 4; stools/day | | | |
| Mean (±SD) | −1.7 (1.92) | −2.5 (2.45) | 0.0116 |
| Median | −2.0 | −2.5 | |
| Min, Max | −5, 5 | −10, 2 | |

Abbreviations:
ITT = intent-to-treat;
Max = maximum;
Min = minimum,
SD = standard deviation.
$^a$P-value for baseline mean comparison is from generalized linear model with analysis center as a covariate. P-value for baseline percentage comparison is from CMH test with analysis center as a covariate. The estimates and p values are from the generalized linear model for the change from baseline result, with independent variables: treatment, analysis center, baseline category (value = Low for ≤5/day and High for >5/day in stool frequency), and the interaction between treatment and baseline category (if p value > 0.15, the interaction term was not included).

The crofelemer group had significantly greater decreases in stool frequency from baseline to Day 2 (p=0.0223) and from baseline to Day 3 (p=0.0140) compared with placebo.

Daily Gastrointestinal Symptom Score

In a repeated measures analysis of longitudinal data over the course of the in-patient period (i.e., changes from baseline at each day during Days 1-4), a statistical trend indicating greater improvements in DGIS scores was observed in the crofelemer group compared with placebo (p=0.0559).

Stool Chloride Concentrations

Stool chloride concentrations were measured in this study because the antisecretory, antidiarrheal effect of crofelemer is likely due to the inhibition of CFTR channel and CACC in the GI lumen; this inhibition blocks luminal Cl$^-$ secretion and accompanying high volume water loss in secretory diarrhea (Fischer 2004; Tradtrantip 2010); thus reduced luminal Cl$^-$ secretion should result in lower stool chloride concentrations. Subjects in the crofelemer group had significantly greater reductions in stool chloride concentrations from baseline to Day 4 when compared with placebo (p=0.0024 by generalized linear model) among subjects with stool chloride data (placebo n=25, crofelemer n=26). Mean (±SD) changes from baseline to Day 4 were 0.123 (0.7138) mg/g in the placebo group and −0.245 (0.5556) mg/g in the crofelemer group.

All publications, patents, and patent applications cited herein are hereby incorporated herein by reference in their entirety.

What is claimed is:

1. A method of treating stool consistency in an HIV positive subject, comprising:
   administering about 250 mg of crofelemer per day to the HIV positive subject.

2. A method of improving stool consistency in an HIV positive subject, comprising:
   administering about 250 mg of crofelemer per day to the HIV positive subject.

3. A method of alleviating watery diarrhea in an HIV positive subject, comprising:
   administering about 250 mg of crofelemer per day to the HIV positive subject.

4. A method of decreasing the number of bowel movements per day in an HIV positive subject, comprising:
   administering about 250 mg of crofelemer per day to the HIV positive subject.

5. The method of any one of claim 1, 2, 3 or 4 wherein the administering is from between about 1 month and about 6 months.

6. The method of any one of claim 1, 2, 3 or 4 wherein the administering is from between about 3 days and 6 months.

7. The method of any one of claim 1, 2, 3 or 4 wherein improvement of symptoms begins on day 3.

8. The method of any one of claim 1, 2, 3 or 4 wherein improvement of symptoms increases with a longer duration of administration after day 3.

9. The method of any one of claim 1, 2, 3 or 4 wherein the subject is of Caucasian or Hispanic descent.

10. The method of any one of claim 1, 2, 3 or 4 wherein the crofelemer is administered for at least 8 days.

11. The method of any one of claim 1, 2, 3 or 4 wherein the crofelemer is administered from between 8 days and 24 weeks.

12. The method of any one of claim 1, 2, 3 or 4 wherein the administering is for about 6 months.

13. The method of any one of claim 1, 2, 3 or 4 wherein the administering is about 6 months or longer.

14. The method of any one of claim 1, 2, 3 or 4 wherein the administering is for the duration of the HIV infection.

15. The method of any one of claim 1, 2, 3 or 4 wherein the response to treatment increases after the crofelemer has been administered for longer than 4 months.

16. The method of any one of claim 1, 2, 3 or 4 wherein the subject is considered treated if the subject demonstrates one or more of: a decrease in the number of bowel movements per day, a decrease in the number of watery bowel movements per day, an improvement in the daily abdominal score for pain or discomfort, an improvement in the score for daily stool consistency, a decrease in stool consistency, a decrease in the number of days per week that subjects experienced urgency, a decrease in the number of days per week that subjects experienced fecal incontinence, or a decrease in the unscheduled visit for a significant worsening of diarrhea.

17. The method of claim 1, wherein subject is considered treated if the subject demonstrates an improvement in the score for daily stool consistency.

18. The method of claim 2, wherein subject is considered treated if the subject demonstrates a decrease in stool consistency.

19. The method of claim 3, wherein subject is considered treated if the subject demonstrates a decrease in the number of watery bowel movements per day.

20. The method of claim 4, wherein subject is considered treated if the subject demonstrates a decrease in the number of bowel movements per day.

21. The method of claim 16, wherein symptoms increased or decreased are measured from a baseline.

22. A method of decreasing the number of days per week a subject experiences fecal incontinence associated with HIV associated diarrhea or HAART associated diarrhea, comprising: administering about 250 mg of crofelemer per day to the subject experiencing fecal incontinence associated with HIV or HAART.

23. The method of claim 1, comprising administering about 125 mg of crofelemer to the subject two times per day.

24. The method of claim 2, comprising administering about 125 mg of crofelemer to the subject two times per day.

25. The method of claim 3, comprising administering about 125 mg of crofelemer to the subject two times per day.

26. The method of claim 4, comprising administering about 125 mg of crofelemer to the subject two times per day.

27. The method of claim 22, comprising administering about 125 mg of crofelemer to the subject two times per day.

* * * * *